(12) United States Patent
Ogunwobi et al.

(10) Patent No.: US 10,947,535 B2
(45) Date of Patent: Mar. 16, 2021

(54) METHODS OF USING PVT1 EXON 9 TO DIAGNOSE AND TREAT PROSTATE CANCER

(71) Applicant: Research Foundation of the City University of New York, New York, NY (US)

(72) Inventors: Olorunseun O. Ogunwobi, Yonkers, NY (US); Adeodat Ilboudo, Bronx, NY (US); Chunxiao Ying, Forest Hills, NY (US)

(73) Assignee: Research Foundation of the City University of New York, New York, NY (US)

( * ) Notice: Subject to any disclaimer, the term of this patent is extended or adjusted under 35 U.S.C. 154(b) by 74 days.

(21) Appl. No.: 16/504,078

(22) Filed: Jul. 5, 2019

(65) Prior Publication Data
US 2019/0382768 A1    Dec. 19, 2019

Related U.S. Application Data

(62) Division of application No. 15/829,263, filed on Dec. 1, 2017, now Pat. No. 10,344,283, which is a division of application No. 15/345,463, filed on Nov. 7, 2016, now Pat. No. 9,845,472.

(60) Provisional application No. 62/300,961, filed on Feb. 29, 2016, provisional application No. 62/251,210, filed on Nov. 5, 2015.

(51) Int. Cl.
*C12Q 1/68* (2018.01)
*C12N 15/113* (2010.01)
*C12Q 1/686* (2018.01)
*C12Q 1/6886* (2018.01)

(52) U.S. Cl.
CPC .......... *C12N 15/1135* (2013.01); *C12Q 1/686* (2013.01); *C12Q 1/6886* (2013.01); *C12N 2310/113* (2013.01); *C12N 2310/14* (2013.01); *C12N 2310/50* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,250,496 B2 * | 7/2007 | Bentwich | G16B 20/00 536/23.1 |
| 7,482,117 B2 * | 1/2009 | Cargill | A61P 9/10 435/6.14 |

(Continued)

OTHER PUBLICATIONS

Meyer et al., A functional variant at a prostate cancer predisposition locus at 8q24 is associated with PVT1 expression, PLoS Genet. Jul. 2011;7(7):e1002165. doi: 10.1371/journal.pgen.1002165. Epub Jul. 21, 2011.*

(Continued)

*Primary Examiner* — Aaron A Priest
(74) *Attorney, Agent, or Firm* — Peter J. Mikesell; Schmeiser, Olsen & Watts, LLP

(57) ABSTRACT

PVT1 exon 9 is overexpressed in aggressively tumorigenic prostate cancer cell lines and prostate tumor tissues. This exon provides a diagnostic tool for the detection and monitoring of aggressive prostate cancer. Several small interfering ribonucleic acids (siRNAs) are disclosed that are useful for treating prostate cancer.

4 Claims, 17 Drawing Sheets

Specification includes a Sequence Listing.

(56) References Cited

U.S. PATENT DOCUMENTS

2011/0287010 A1 11/2011 Assinder et al.
2014/0065620 A1 3/2014 Perez et al.

OTHER PUBLICATIONS

ThermoFisher, TaqMan Assay Hs00413039_m1, available at https://www.thermofisher.com/order/genome-database/?pearUXVerSuffix=pearUX2&elcanoForm=true#!/ge/assays/ge_all/?keyword=Hs00413039&searchMethod=keyword, accessed Feb. 25, 2019.*
Ilboudo, A. et al; PVT1 Exon 9: A Potential Biomarker of Aggressive Prostate Cancer?; International Journal of Environmental Research and Public Health; Dec. 22, 2015; pp. 1-13; 13, 12; MDPI.
Huppi, K. et al; The 8q24 gene desert: an oasis of non-coding transcriptional activity; Frontiers in Genetics; Apr. 30, 2012; pp. 1-11; vol. 3, Article 69.
*Homo sapiens* Pvt1 oncogene; Accession No. BC033663 from DNA Bank of Japan downloaded Aug. 10, 2018.
Mammallian Gene Collection (MGC) Program Team; Generation and initial analysis of more than 15,000 full-length human and mouse cDNA sequences; Dec. 24, 2002; pp. 16899-16903; vol. 99, No. 26.
USPTO; Non-Final Office Action dated Jun. 28, 2018 for U.S. Appl. No. 15/829,263.
Meyer, K. et al.; A Functional Variant at a Prostate Cancer Predisposition; Locus at 8q24 Is Associated with PCT1 Expression; Jul. 21, 2011; 11 pages; vol. 7, Issue 7.

* cited by examiner

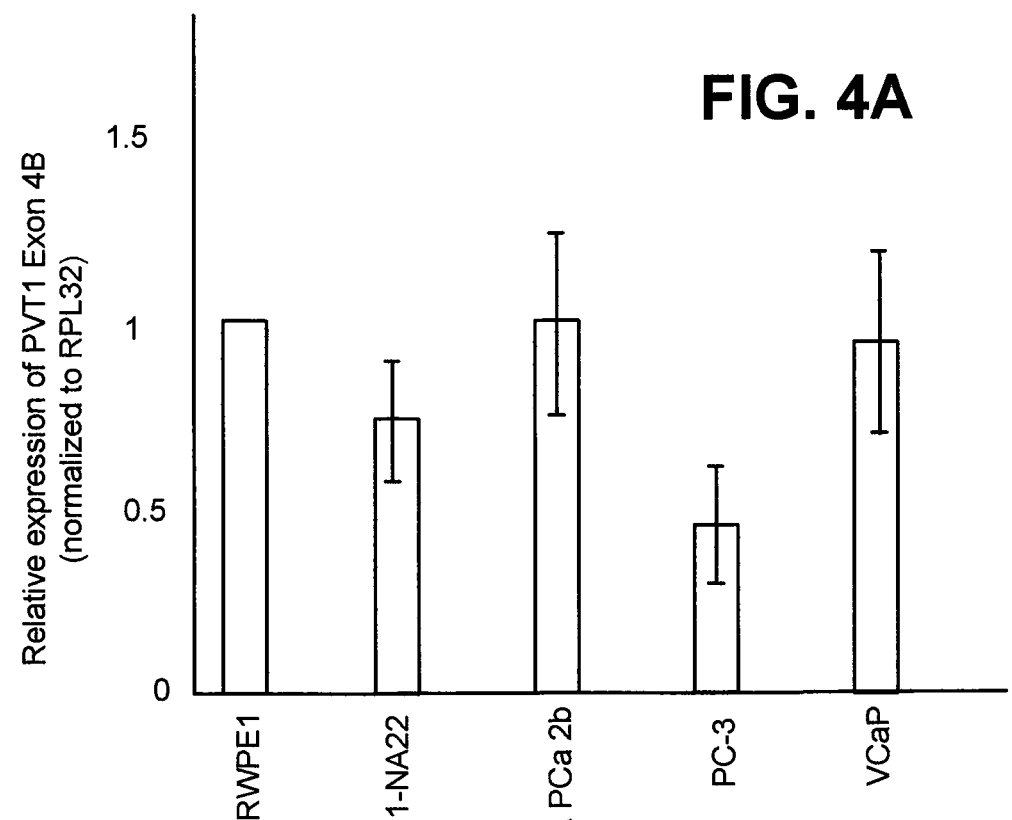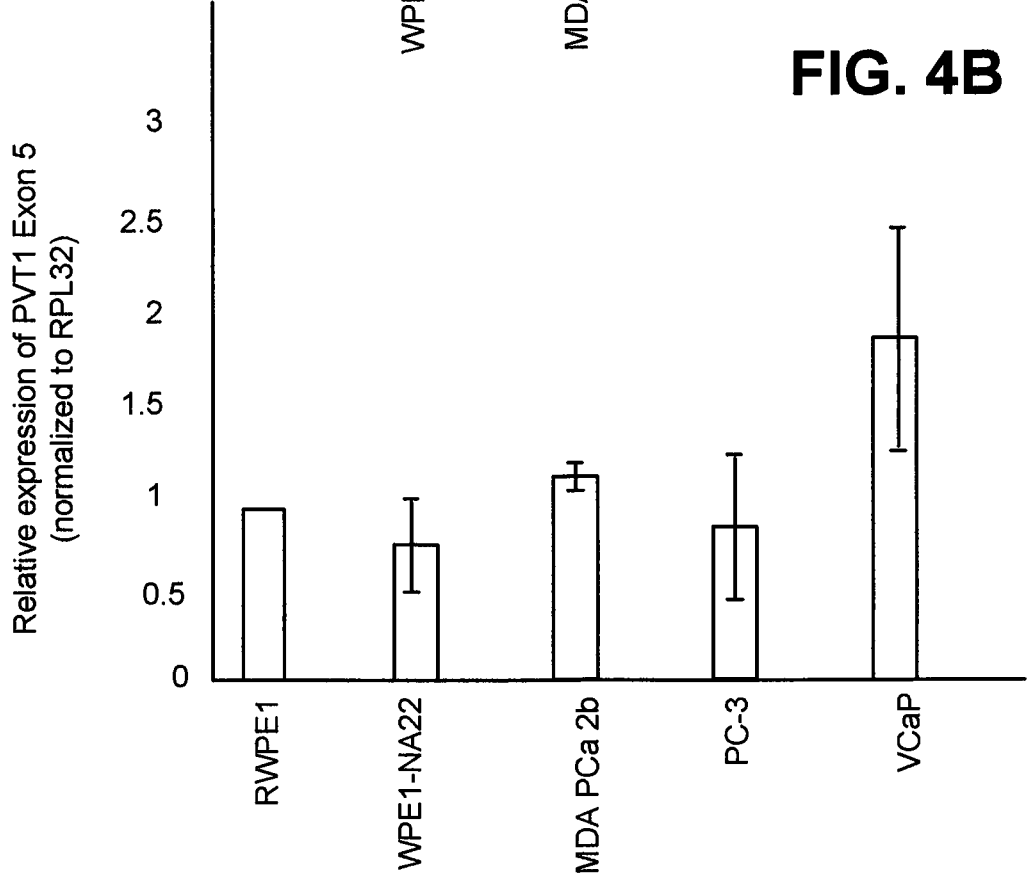

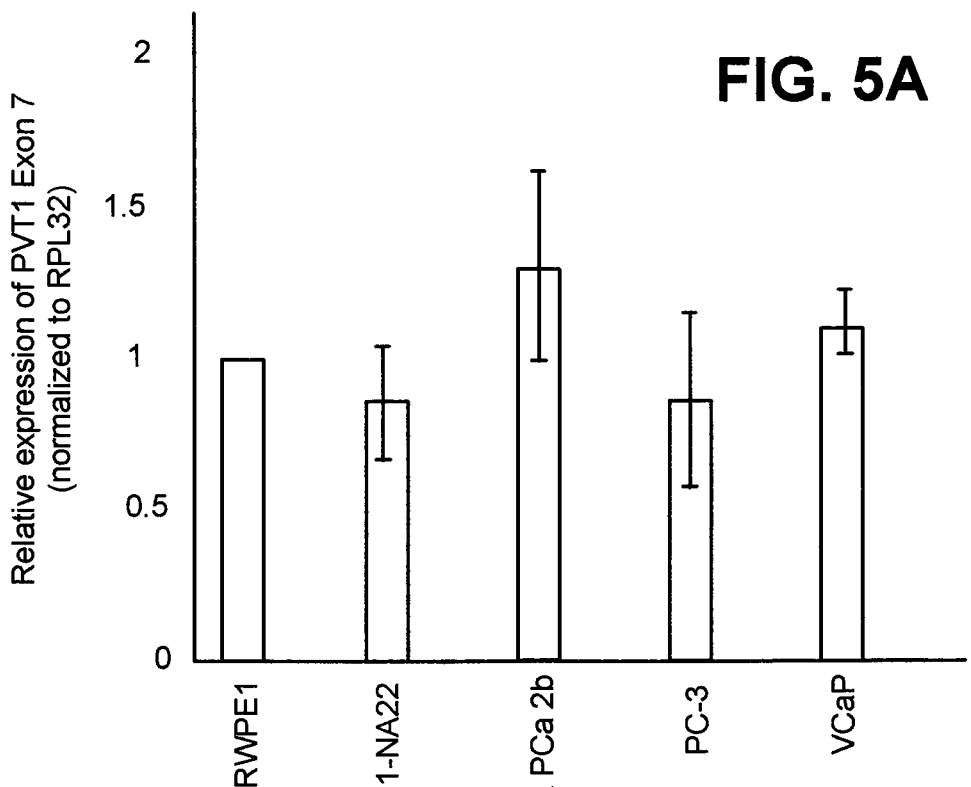
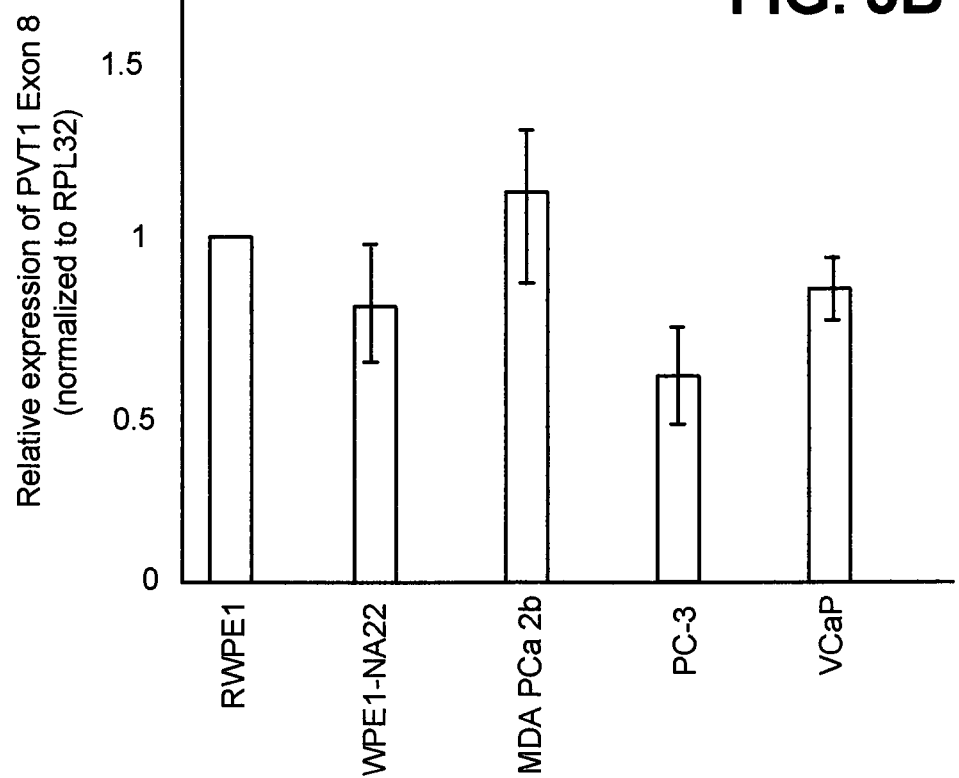

SEQUENCE LISTING

<160> NUMBER OF SEQ ID NOS: 37

<210> SEQ ID NO 1
<211> LENGTH: 18
<212> TYPE: DNA
<213> ORGANISM: Artificial Sequence
<220> FEATURE:
<223> OTHER INFORMATION: Forward primer for PVT1 Exon 1A

<400> SEQUENCE: 1
acgagctgcg agcaaaga                                                   18

<210> SEQ ID NO 2
<211> LENGTH: 20
<212> TYPE: DNA
<213> ORGANISM: Artificial Sequence
<220> FEATURE:
<223> OTHER INFORMATION: Reverse primer for PVT1 Exon 1A

<400> SEQUENCE: 2
cgtgtctcca caggtcacag                                                 20

<210> SEQ ID NO 3
<211> LENGTH: 21
<212> TYPE: DNA
<213> ORGANISM: Artificial Sequence

```
<220> FEATURE:
<223> OTHER INFORMATION: Forward primer for PVT1 Exon 1B

<400> SEQUENCE: 3
cggaagctgc agaaggacaa a                                          21

<210> SEQ ID NO 4
<211> LENGTH: 23
<212> TYPE: DNA
<213> ORGANISM: Artificial Sequence
<220> FEATURE:
<223> OTHER INFORMATION: Reverse primer for PVT1 Exon 1B

<400> SEQUENCE: 4
ctcaaataat ggagaccagg cca                                        23

<210> SEQ ID NO 5
<211> LENGTH: 20
<212> TYPE: DNA
<213> ORGANISM: Artificial Sequence
<220> FEATURE:
<223> OTHER INFORMATION: Forward primer for PVT1 Exon 1C

<400> SEQUENCE: 5
gcagtgcagg aagccaacta                                            20

<210> SEQ ID NO 6
<211> LENGTH: 22
<212> TYPE: DNA
<213> ORGANISM: Artificial Sequence
<220> FEATURE:
<223> OTHER INFORMATION: Reverse primer for PVT Exon 1C

<400> SEQUENCE: 6
cttaggggtc cttacagcca ag                                         22

<210> SEQ ID NO 7
<211> LENGTH: 20
<212> TYPE: DNA
<213> ORGANISM: Artificial Sequence
<220> FEATURE:
<223> OTHER INFORMATION: Forward primer for PVT1 Exon 2

<400> SEQUENCE: 7
aaccatgcac tggaatgaca                                            20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for PVT1 Exon 2

<400> SEQUENCE: 8
catcagatgc ttcaccagga                                            20

<210> SEQ ID NO 9
<211> LENGTH: 21
<212> TYPE: DNA
<213> ORGANISM: Artificial Sequence
<220> FEATURE:
<223> OTHER INFORMATION: Forward primer for PVT1 Exon 3B

<400> SEQUENCE: 9
catactccct ggagccttct c                                          21
```

```
<210> SEQ ID NO 10
<211> LENGTH: 21
<212> TYPE: DNA
<213> ORGANISM: Artificial Sequence
<220> FEATURE:
<223> OTHER INFORMATION: Reverse primer for PVT1 Exon 3B

<400> SEQUENCE: 10
cagtgtcctg gcagtaaaag g                                              21

<210> SEQ ID NO 11
<211> LENGTH: 20
<212> TYPE: DNA
<213> ORGANISM: Artificial Sequence
<220> FEATURE:
<223> OTHER INFORMATION: Forward primer for PVT1 Exon 4A

<400> SEQUENCE: 11
gggttcaagt gatcctcctg                                                20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for PVT1 Exon 4A

<400> SEQUENCE: 12
tgtaatccca gcacgttgaa                                                20

<210> SEQ ID NO 13
<211> LENGTH: 20
<212> TYPE: DNA
<213> ORGANISM: Artificial Sequence
<220> FEATURE:
<223> OTHER INFORMATION: Forward primer for PVT1 Exon 4B

<400> SEQUENCE: 13
cacctgggat ttaggcactt                                                20

<210> SEQ ID NO 14
<211> LENGTH: 24
<212> TYPE: DNA
<213> ORGANISM: Artificial Sequence
<220> FEATURE:
<223> OTHER INFORMATION: Reverse primer for PVT1 Exon 4B

<400> SEQUENCE: 14
ccaatctcaa aatactccag cttt                                           24

<210> SEQ ID NO 15
<211> LENGTH: 24
<212> TYPE: DNA
<213> ORGANISM: Artificial Sequence
<220> FEATURE:
<223> OTHER INFORMATION: Forward primer for PVT1 Exon 5

<400> SEQUENCE: 15
gccaacagag attttgagaa acac                                           24

<210> SEQ ID NO 16
<211> LENGTH: 20
<212> TYPE: DNA
<213> ORGANISM: Artificial Sequence
<220> FEATURE:
<223> OTHER INFORMATION: Reverse primer for PVT1 Exon 5
```

```
<400> SEQUENCE: 16
tcagctcagg ttcccattgt                                                    20

<210> SEQ ID NO 17
<211> LENGTH: 21
<212> TYPE: DNA
<213> ORGANISM: Artificial Sequence
<220> FEATURE:
<223> OTHER INFORMATION: Forward primer for PVT1 Exon 6

<400> SEQUENCE: 17
tgctagggtg acagaaactg g                                                  21

<210> SEQ ID NO 18
<211> LENGTH: 20
<212> TYPE: DNA
<213> ORGANISM: Artificial Sequence
<220> FEATURE:
<223> OTHER INFORMATION: Reverse primer for PVT1 Exon 6

<400> SEQUENCE: 18
cccaggtctt gatgacaggt                                                    20

<210> SEQ ID NO 19
<211> LENGTH: 20
<212> TYPE: DNA
<213> ORGANISM: Artificial Sequence
<220> FEATURE:
<223> OTHER INFORMATION: Forward primer for PVT1 Exon 7

<400> SEQUENCE: 19
ttggtgctct gtgttcacct                                                    20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for PVT1 Exon 7

<400> SEQUENCE: 20
tgtccactag cagcaacagg                                                    20

<210> SEQ ID NO 21
<211> LENGTH: 20
<212> TYPE: DNA
<213> ORGANISM: Artificial Sequence
<220> FEATURE:
<223> OTHER INFORMATION: Forward primer for PVT1 Exon 8

<400> SEQUENCE: 21
agaataacgg gctcccagat                                                    20

<210> SEQ ID NO 22
<211> LENGTH: 20
<212> TYPE: DNA
<213> ORGANISM: Artificial Sequence
<220> FEATURE:
<223> OTHER INFORMATION: Reverse primer for PVT1 Exon 8

<400> SEQUENCE: 22
aagctgggtc ttcatcctga                                                    20

<210> SEQ ID NO 23
```

```
<211> LENGTH: 20
<212> TYPE: DNA
<213> ORGANISM: Artificial Sequence
<220> FEATURE:
<223> OTHER INFORMATION: Forward primer for PVT1 Exaon 9

<400> SEQUENCE: 23
catgactcca cctggacctt                                                    20

<210> SEQ ID NO 24
<211> LENGTH: 19
<212> TYPE: DNA
<213> ORGANISM: Artificial Sequence
<220> FEATURE:
<223> OTHER INFORMATION: Reverse primer for PVT1 Exon 9

<400> SEQUENCE: 24
gtgggcgatg aagttcgta                                                     19

<210> SEQ ID NO 25
<211> LENGTH: 273
<212> TYPE: DNA
<213> ORGANISM: Homo sapiens

<400> SEQUENCE: 25 gtttttgca tgtctgacac ccatgactcc acctggacct tatggctcca cccagaagca        60
attcagccca acaggaggac agcttcaacc cattacgatt tcatctctgc cccaaccact      120
cagcagcaag cacctgttac ctgtccaccc caccccttc ccccaaactg cctttgaaaa       180
atccctaacc tatgagcttt gaataagatg agtacgaact tcatcgccca cgtggcgtgg     240
ccggcctcgt gtctattaaa ttcttttttct act                                  273

<210> SEQ ID NO 26
<211> LENGTH: 21
<212> TYPE: RNA
<213> ORGANISM: Artificial Sequence
<220> FEATURE:
<223> OTHER INFORMATION: Forward sequence of an siRNA

<400> SEQUENCE: 26
cuucaaccca uuacgauuuu u                                                  21

<210> SEQ ID NO 27
<211> LENGTH: 21
<212> TYPE: RNA
<213> ORGANISM: Artificial Sequence
<220> FEATURE:
<223> OTHER INFORMATION: Reverse strand of SEQ ID NO: 26

<400> SEQUENCE: 27
aaaucguaau ggguugaagu u                                                  21

<210> SEQ ID NO 28
<211> LENGTH: 21
<212> TYPE: RNA
<213> ORGANISM: Artificial Sequence
<220> FEATURE:
<223> OTHER INFORMATION: Forward sequence of an siRNA

<400> SEQUENCE: 28
ggacagcuuc aacccauuau u                                                  21

<210> SEQ ID NO 29
<211> LENGTH: 21
```

```
<212> TYPE: RNA
<213> ORGANISM: Artificial Sequence
<220> FEATURE:
<223> OTHER INFORMATION: Reverse sequence of SEQ ID NO: 28

<400> SEQUENCE: 29
uaauggguug aagcuguccu u                                              21

<210> SEQ ID NO 30
<211> LENGTH: 21
<212> TYPE: RNA
<213> ORGANISM: Artificial Sequence
<220> FEATURE:
<223> OTHER INFORMATION: Forward sequence of an siRNA

<400> SEQUENCE: 30
aggacagcuu caacccauuu u                                              21

<210> SEQ ID NO 31
<211> LENGTH: 21
<212> TYPE: RNA
<213> ORGANISM: Artificial Sequence
<220> FEATURE:
<223> OTHER INFORMATION: Reverse sequence of SEQ ID NO: 30

<400> SEQUENCE: 31
aauggguuga agcuguccuu u                                              21

<210> SEQ ID NO 32
<211> LENGTH: 21
<212> TYPE: RNA
<213> ORGANISM: Artificial Sequence
<220> FEATURE:
<223> OTHER INFORMATION: Forward sequence of an siRNA

<400> SEQUENCE: 32
ccauuacgau uucaucucuu u                                              21

<210> SEQ ID NO 33
<211> LENGTH: 20
<212> TYPE: RNA
<213> ORGANISM: Artificial Sequence
<220> FEATURE:
<223> OTHER INFORMATION: Reverse sequence of SEQ ID NO: 32

<400> SEQUENCE: 33
agagaugaaa ucguaauggu                                                20

<210> SEQ ID NO 34
<211> LENGTH: 21
<212> TYPE: RNA
<213> ORGANISM: Artificial Sequence
<220> FEATURE:
<223> OTHER INFORMATION: Forward sequence of an siRNA

<400> SEQUENCE: 34 accaugagc uuugaauaau u                                               21

<210> SEQ ID NO 35
<211> LENGTH: 21
<212> TYPE: RNA
<213> ORGANISM: Artificial Sequence
<220> FEATURE:
<223> OTHER INFORMATION: Reverse sequence for SEQ ID NO: 34

<400> SEQUENCE: 35
```

```
uuauucaaag cucauagguu u                                              21

<210> SEQ ID NO 36
<211> LENGTH: 301
<212> TYPE: DNA
<213> ORGANISM: Homo sapiens

<400> SEQUENCE: 36
agtctcactc tgtggtccag gctgaagtac agtggcatga tcccaggtca ctgcaacccc     60
cacctcccgg gttcaagtga tcctcctgcc tcagcctccc gagtagctgg tattacaggc    120
gtgtgccaca aagcctggct aagttttgta tttttagtag agacggggtt tcaccatgtt    180
ggccaggttg gtctcgaact cctgacctca agtgatccac tcactttggc ctttcaacgt    240
gctgggatta caggcgagag tcaccgcacc cggacgactc tgacattttt gaagagtcca    300
g                                                                    301

<210> SEQ ID NO 37
<211> LENGTH: 130
<212> TYPE: DNA
<213> ORGANISM: Homo sapiens

<400> SEQUENCE: 37
aatcctgtta cacctgggat ttaggcactt tcaatctgaa aaaatacata tcctttcagc     60
actctggacg gacttgagaa ctgtccttac gtgacctaaa gctggagtat tttgagattg    120
gagaattaag                                                           130
```

METHODS OF USING PVT1 EXON 9 TO DIAGNOSE AND TREAT PROSTATE CANCER

CROSS-REFERENCE TO RELATED APPLICATIONS

This application is a divisional of U.S. patent application Ser. No. 15/829,263 (filed Dec. 1, 2017) which is a divisional of U.S. patent application Ser. No. 15/345,463 (filed Nov. 7, 2016) which claims priority to and is a nonprovisional of U.S. Patent Applications 62/251,210 (filed Nov. 5, 2015) and 62/300,961 (filed Feb. 28, 2015), the entirety of which are incorporated herein by reference.

STATEMENT OF FEDERALLY SPONSORED RESEARCH OR DEVELOPMENT

This invention was made with Government support under grant numbers G12 MD007599 awarded by the National Institute on Minority Health and Heal Disparities. The government has certain rights in the invention.

REFERENCE TO A SEQUENCE LISTING

This application contains a Sequence Listing in computer readable form. The computer readable form is incorporated herein by reference.

BACKGROUND OF THE INVENTION

Prostate cancer (PCa) is the most common non-cutaneous cancer and the second leading cause of cancer-related death for men in the U.S. It is estimated that, in 2015, approximately 220,800 new cases of PCa will be diagnosed and 27,540 deaths will result from PCa. African Americans have the highest incidence of PCa in the world, with an annual average of 229 per 100,000 men for the period of 2006-2010, which represents about two-fold more than Caucasian Americans. PCa is also the leading cancer in terms of incidence and mortality in men from Africa and the Caribbean. Consequently, African ancestry is a very important risk factor.

PCa is a heterogeneous disease, with multiple risks factors. The specific reasons for poor outcomes from PCa in males of African ancestry (MoAA) when compared to Caucasian males (CM) are not understood. However, it is widely believed that the causes of PCa disparities are complex and multifaceted. Two potential reasons are frequently proposed to explain this profound disparity in PCa: (1) MoAA present more often than CM with advanced incurable PCa due to more limited access to health care; (2) PCa is biologically more aggressive in MoAA than CM, and can be attributed to environmental and/or genetic risk factors.

The 8q24 human chromosomal region is one of the most important susceptibility genetic loci for PCa. Several studies have identified single nucleotide polymorphisms (SNPs) located in chromosome 8q24 as susceptibility markers for PCa. The 8q24 chromosomal region has only one protein-coding gene, the well-known MYC oncogene implicated in different cancers, including PCa. However, it also has a number of non-protein coding genes (such as PVT1) whose functional roles have not been thoroughly investigated yet.

In recent years, non-protein coding RNAs (ncRNAs) have received special attention because they have been identified in many studies as being important in cancer biology. Substantial progress has been made in understanding the role of small non-coding RNAs such as microRNAs (miRNAs) in the development and progression of cancers. However, studying the role of long non-coding RNAs (lncRNAs) in cancers appears to be more complicated. LncRNAs are defined as endogenous cellular RNAs that have a size of more than 200 nucleotides and that do not possess an extended open reading frame.

The discussion above is merely provided for general background information and is not intended to be used as an aid in determining the scope of the claimed subject matter.

BRIEF DESCRIPTION OF THE INVENTION

PVT1 exon 9 is overexpressed in aggressively tumorigenic prostate cancer cell lines and prostate tumor tissues. This exon provides a diagnostic tool for the detection and monitoring of aggressive prostate cancer. Several small interfering ribonucleic acids (siRNAs) are disclosed that are useful for treating prostate cancer.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 4A to FIG. 4C are graphs depicting expression of PVT1 exons 4b, 5, 6 (FIG. 4A, FIG. 4B and FIG. 4C, respectively);

FIG. 5A and FIG. 5B are graphs depicting expression of exons 7 and 8, respectively;

DETAILED DESCRIPTION OF THE INVENTION

Prostate cancer has been shown to be associated with single nucleotide polymorphisms around regions 2 and 3 of the 8q24 human chromosomal region. The non-protein coding gene locus Plasmacytoma Variant Translocation 1 (PVT1) is located at 8q24 and is overexpressed in PCa and, therefore, is also a candidate biomarker to explain the well-known disparity among males of African ancestry. PVT1 has at least twelve exons that make separate transcripts which may have different functions, all of which are, at present unknown, in PCa. The disclosed study determined if any PVT1 transcripts play a role in aggressiveness and racial disparity in PCa. A panel of seven PCa cell lines was used, including three derived from males of African ancestry. Ribonucleic acid extraction, complementary deoxyribonucleic acid synthesis, and quantitative polymerase chain reaction (qPCR) were performed to evaluate expression of all twelve PVT1 exons. Each qPCR was performed in quadruplicates. At least four separate qPCR experiments were performed. Expression of PVT1 exons was inconsistent except for exon 9. There was no significant difference in exon 9 expression between cell lines derived from Caucasian males (CM), and an indolent cell line derived from males of African ancestry. However, exon 9 expression in the aggressive MDA PCa 2b and E006AA-hT cell lines derived from males of African ancestry was significantly higher than in other cell lines. Consequently, differential expression of exon 9 of PVT1 was observed in a manner that suggests that PVT1 exon 9 may be associated with aggressive PCa in males of African ancestry.

Figure 1:
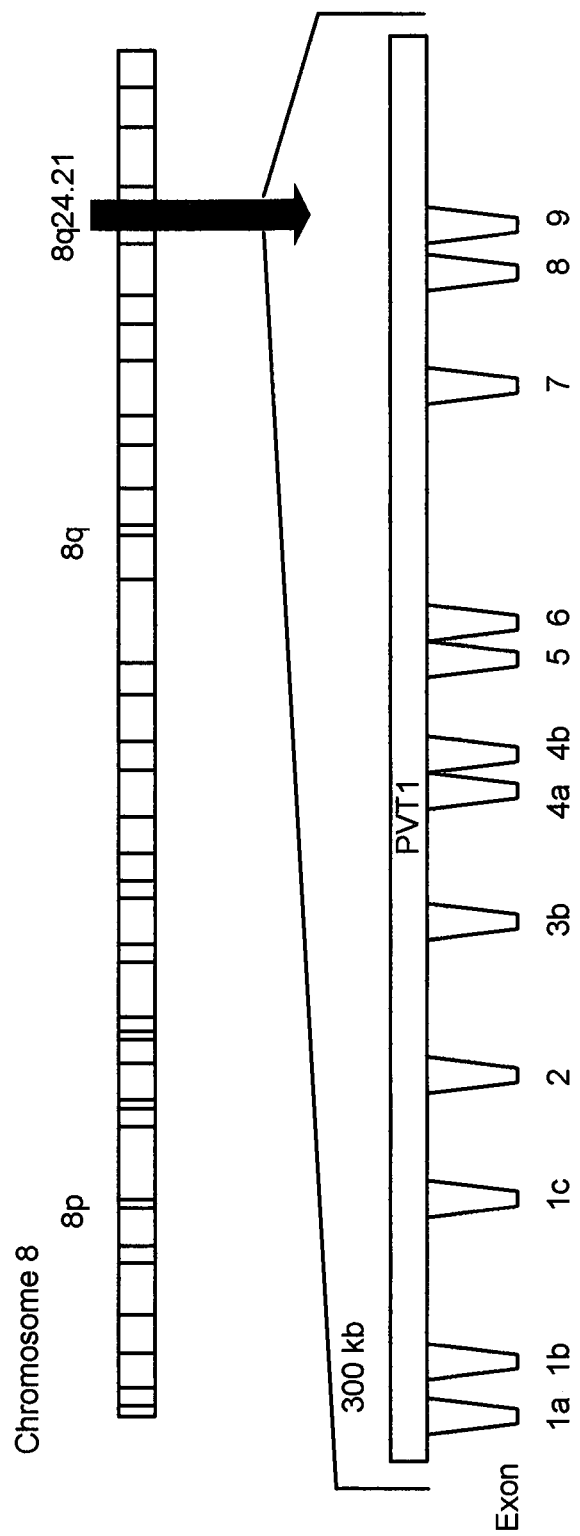
FIG. 1 is schematic depiction of the PCa susceptibility locus.

FIG. 1 depicts the PCa susceptibility locus. The PVT1 gene locus expresses several alternatively spliced non-protein coding transcripts and it also encodes a cluster of microRNAs. However, no specific functional role for any of these transcripts has been identified. PVT1 is located downstream of MYC. It has a size of over 300 kb and, since its discovery in the mid-80s, it has been proven to play an important role in cancer. The upregulation of PVT1 has been found to be involved in poor prognosis in colorectal cancer and gastric cancer. In non-small cell lung cancer, it promotes tumorigenesis. In PCa, PVT1 has been found to have an increased expression in comparison to normal prostate tissue with the presence of a newly identified functional PCa specific genetic variant, rs378854. PVT1 encodes for several transcripts, approximately twelve exons, and their differential expression has not previously been investigated. Consequently, in the present disclosure data on the relative expression of the twelve different exons of PVT1 in models representative of a wide variety of clinical PCa. Observations indicate that exon 9 of PVT1 is significantly overexpressed in PCa derived from aggressive PCa in MoAA, thus suggesting the potential for clinical utility in this population group least served by current management strategies.

Cell Lines

For this study, seven prostate epithelial cell lines were used, in representation of the heterogeneity notable in clinical PCa. The RWPE1 cells are epithelial cells derived from the peripheral zone of a histologically normal prostate from a 54-year-old CM. The cells were later transfected with a single copy of the human papilloma virus 18 (HPV-18) to finally establish the cell line. RWPE1 is non-tumorigenic. WPE1-NA22 cells were obtained by exposing RWPE1 to N-methyl-N-nitrosourea. WPE1-NA22 cells are mildly tumorigenic. MDA PCa 2b cells were derived from bone metastasis of prostate adenocarcinoma in a 64-year-old MoAA. PC-3 was derived from bone metastasis of a grade IV prostatic adenocarcinoma from a 62-year-old CM. The VCaP cell line was established from a vertebral bone metastasis from a 59-year-old CM with hormone refractory PCa. The E006AA cell line was established from a 50-year-old MoAA who underwent radical retropubic prostatectomy for treatment of clinically-localized PCa. The E006AA cell line is non-tumorigenic in nude mice. The highly tumorigenic derivative of E006AA, the E006AA-hT cell line, was established and characterized in 2014. The main features of all the cell lines used in this study are summarized in Table 1.

All the cell lines were purchased from the American Type Culture Collection (ATCC, Manassas, Va., USA) except for the E006AA and E006AA-hT cell lines that were a kind gift from Dr. Shariar Koochekpour of the Roswell Park Cancer Institute (New York, USA).

TABLE 1

Main characteristics of prostate epithelial cell lines used in this study

| Cell line | CM | MoAA | Indolent Disease | Aggressive Disease | Normal Prostate | Androgen Status |
|---|---|---|---|---|---|---|
| RWPE1 | X | | | | X | Dependent |
| WPE1-NA22 | X | | X | | | Dependent |
| MDA PCa 2b | | X | | X | | Dependent |
| E006AA | | X | X | | | Independent |
| E0006AA-hT | | X | | X | | Independent |
| PC-2 | X | | | X | | Independent |
| VCaP | X | | | X | | Dependent |

Cell Culture and Cell Culture Reagents

RWPE1 and WPE1-NA22 cells were maintained in Keratinocyte-Serum Free Medium (Life Technologies, Grand Island, N.Y., USA) supplemented with 0.05 mg/mL bovine pituitary extract and 5 ng/mL human Epidermal Growth Factor. MDA PCa 2b cells were maintained in F-12K medium supplemented with 20% fetal bovine serum (FBS), 25 ng/mL cholera toxin, 10 ng/mL mouse epidermal growth factor, 0.005 mM phosphoethanolamine, 100 pg/mL hydrocortisone, 45 nM selenous acid and 0.005 mg/mL bovine insulin. PC-3 cells were maintained in F-12K medium supplemented with 10% FBS. VCaP cells were maintained in DMEM medium supplemented with 10% FBS. E006AA and E006AA-hT cells were maintained in DMEM medium supplemented with 10% FBS. All cell lines were also cultured with the presence of 1% Penicillin/Streptomycin.

Primer Design and Sequences

The following PVT1 exons were previously described: 1a, 2, 3b, 4b, 7, 8 and 9 (Frontiers in Genetics, 20, Apr. 2012, vol 3, article 69). However, using the UCSC Genome browser, the PVT1 sequence was carefully annotated and twelve exons were retrieved from the analysis. The Primers3 Plus software was used to custom-design primers for all twelve annotated exons, and the sequences of the primers are listed in Table 2.

TABLE 2

List of primer sequences of PVT1 exons

| Primer Name | Primer Sequence 5'-3' |
|---|---|
| PVT1 Exon 1A-F | ACGAGCTGCGAGCAAAGA (SEQ ID NO: 1) |
| PVT1 Exon 1A-R | CGTGTCTCCACAGGTCACAG (SEQ ID NO: 2) |
| PVT1 Exon 1B-F | CGGAAGCTGCAGAAGGACAAA (SEQ ID NO: 3) |
| PVT1 Exon 1B-R | CTCAAATAATGGAGACCAGGCCA (SEQ ID NO: 4) |
| PVT1 Exon 1C-F | GCAGTGCAGGAAGCCAACTA (SEQ ID NO: 5) |
| PVT1 Exon 1C-R | CTTAGGGGTCCTTACAGCCAAG (SEQ ID NO: 6) |
| PVT1 Exon 2-F | AACCATGCACTGGAATGACA (SEQ ID NO: 7) |
| PVT1 Exon 2-R | CATCAGATGCTTCACCAGGA (SEQ ID NO: 8) |
| PVT1 Exon 3B-F | CATACTCCCTGGAGCCTTCTC (SEQ ID NO: 9) |
| PVT1 Exon 3B-R | CAGTGTCCTGGCAGTAAAAGG (SEQ ID NO: 10) |
| PVT1 Exon 4A-F | GGGTTCAAGTGATCCTCCTG (SEQ ID NO: 11) |
| PVT1 Exon 4A-R | TGTAATCCCAGCACGTTGAA (SEQ ID NO: 12) |
| PVT1 Exon 4B-F | CACCTGGGATTTAGGCACTT (SEQ ID NO: 13) |
| PVT1 Exon 4B-R | CCAATCTCAAAATACTCCAGCTTT (SEQ ID NO: 14) |
| PVT1 Exon 5-F | GCCAACAGAGATTTTGAGAAACAC (SEQ ID NO: 15) |
| PVT1 Exon 5-R | TCAGCTCAGGTTCCCATTGT (SEQ ID NO: 16) |
| PVT1 Exon 6-F | TGCTAGGGTGACAGAAACTGG (SEQ ID NO: 17) |
| PVT1 Exon 6-R | CCCAGGTCTTGATGACAGGT (SEQ ID NO: 18) |
| PVT1 Exon 7-F | TTGGTGCTCTGTGTTCACCT (SEQ ID NO: 19) |
| PVT1 Exon 7-R | TGTCCACTAGCAGCAACAGG (SEQ ID NO: 20) |

TABLE 2-continued

List of primer sequences of PVT1 exons

| Primer Name | Primer Sequence 5'-3' |
|---|---|
| PVT1 Exon 8-F | AGAATAACGGGCTCCCAGAT (SEQ ID NO: 21) |
| PVT1 Exon 8-R | AAGCTGGGTCTTCATCCTGA (SEQ ID NO: 22) |
| PVT1 Exon 9-F | CATGACTCCACCTGGACCTT (SEQ ID NO: 23) |
| PVT1 Exon 9-R | GTGGGCGATGAAGTTCGTA (SEQ ID NO: 24) |

RNA Extraction and RT-QPCR

At 75% confluency, total RNA was extracted from cells in a 60×15 mm tissue culture dish, using RNeasy Mini Kit (Qiagen, Germany, cat #74104). After quantification with Nanodrop 1000 spectrophotometer (NanoDrop, Madison, Wis., USA), 1 μg of RNA was reverse-transcribed into cDNA using QuantiTect Reverse Transcription kit (Qiagen, Germany, cat #205311). Amplification reactions were performed in 25 μL reaction volume using SYBR Green PCR master Mix (Life Technologies, Grand Island, N.Y., USA cat #4309155), cDNA template and 0.4 μM final concentration for primers. The thermal cycle profile employed was as follows: 50° C. for 2 min, 10 min initial denaturation at 95° C., and 40 cycles of 15 s denaturation at 94° C., 1 min annealing at 65° C. A dissociation curve was also added at the end of the cycle. The amplifications were carried out on the 7500 Real Time PCR machine (Applied Biosystems instruments, Grand Island, N.Y., USA). Messenger RNA (mRNA) expression was assessed in quadruplicates in at least 3 independent experiments and normalized to RPL32 mRNA expression. Relative expression levels were calculated by the Ct method (ΔΔ Ct). Previously published RPL32 primer sequences were used.

Statistical Analysis

Data are presented as mean±standard error of the mean (S.E.M) of at least three independent experiments. Statistical significance of differences was assessed using two-tailed Student's t test. p values less than 0.05 were deemed significant. A summary of all p values resulting from comparing each prostate cell line to the normal prostate cell line RWPE1 for all PVT1 exons are summarized in Table 3.

TABLE 3

Summary of p values comparing each prostate cell line to the normal prostate cell line RWPE1 for all PVT1 exons

| Caption | WPE1-NA22 | MDA PCa 2b | E006AA | E006AA-hT | PC-3 | VCaP |
|---|---|---|---|---|---|---|
| Exon 1A | 0.4148 | 0.1017 | | | 0.2865 | 0.0262 |
| Exon 1B | 0.2950 | 0.0133 | | | 0.0060 | 0.3158 |
| Exon 1C | 0.2864 | 0.2326 | | | 0.0686 | 0.0369 |
| Exon 2 | 0.3284 | 0.0016 | | | 0.0114 | 0.2598 |
| Exon 3B | 0.4073 | 0.4516 | | | 0.0359 | 0.1179 |
| Exon 4A | 0.4410 | 0.0010 | 0.3320 | 0.2397 | 0.1518 | 0.0633 |
| Exon 4B | 0.0780 | 0.4943 | | | 0.0130 | 0.4064 |
| Exon 5 | 0.1867 | 0.0244 | | | 0.3641 | 0.0938 |
| Exon 6 | 0.1160 | 0.4997 | | | 0.3313 | 0.0409 |
| Exon 7 | 0.1976 | 0.1799 | | | 0.3066 | 0.1383 |
| Exon 8 | 0.1492 | 0.2963 | | | 0.0255 | 0.0650 |
| Exon 9 | 0.0179 | 0.0050 | 0.0742 | 0.0416 | 0.0007 | 0.3552 |

For PVT1 exon 1a and 1c, no significant differential expression was observed in the MDA PCa 2b PCA cell line derived from a male of African ancestry, when compared to the RWPE1 normal prostate epithelial cell line. For PVT1 exon 1b, a decrease in the expression level was observed in the MDA PCa 2b cell line, but it was not significant. For PVT1 exon 2, a small but significant decrease (p value=0.00161) in relative expression by MDA PCa 2b was observed in comparison to RWPE1. However, for PVT1 exon 3b, no difference in relative expression was observed when MDA PCa 2b was compared to RWPE1. For PVT1 exon 4a, a significant decrease in relative expression by MDA PCa 2b of almost 60% in comparison to RWPE1 was observed (p value=0.001104). However, PVT1 Exon 4a was overexpressed in the highly tumorigenic E006AA-hT also derived from a MoAA. However, this overexpression was not statistically significant (p value=0.2397). Given that both MDA PCa 2b and E006AA-hT are highly tumorigenic and derived from MoAA, the dissimilar expression of PVT1 exon 4a in them suggests inconsistency. The reasons for this are currently unclear.

Figures 2A, 2B:
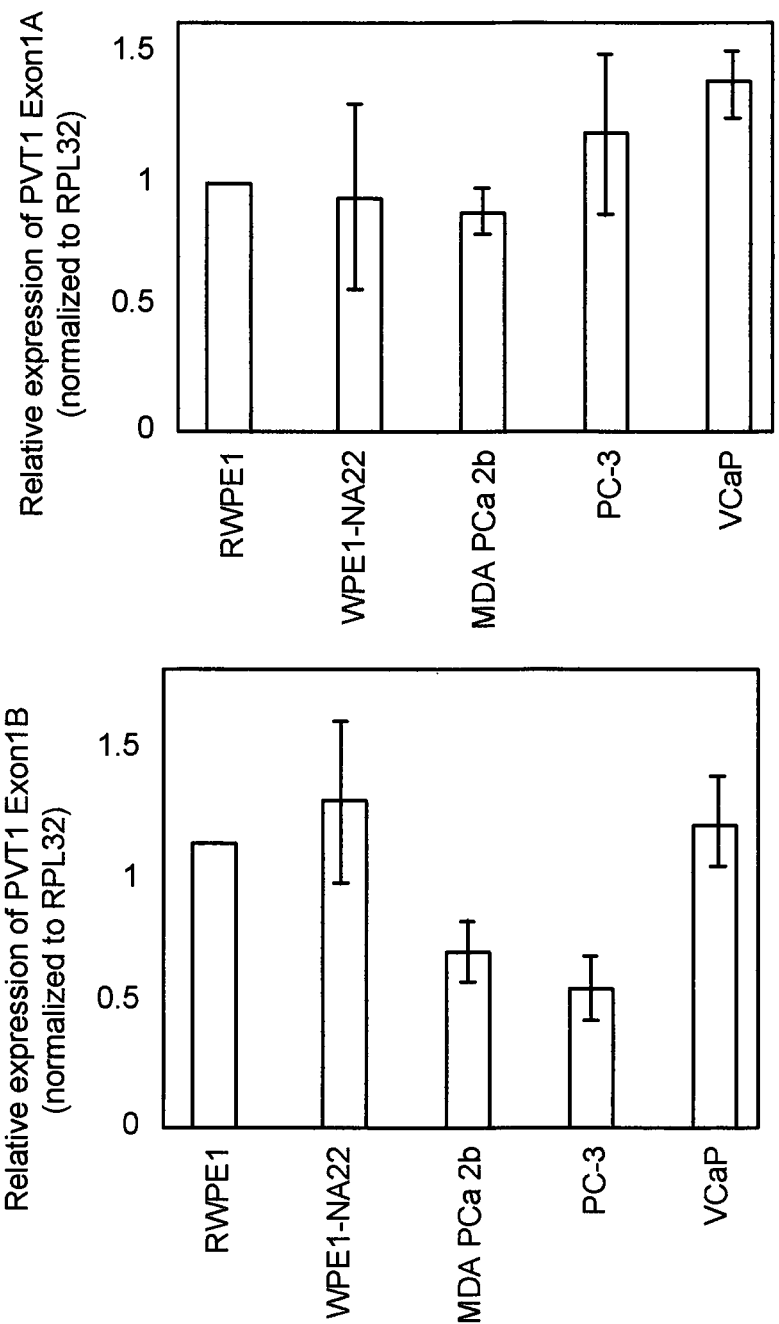
FIG. 2A, FIG. 2B and FIG. 2C are graphs depicting expression of PVT1 exons 1a; 1b and 1c in non-tumorigenic and tumorigenic prostate epithelial cell lines.
Figure 2C:
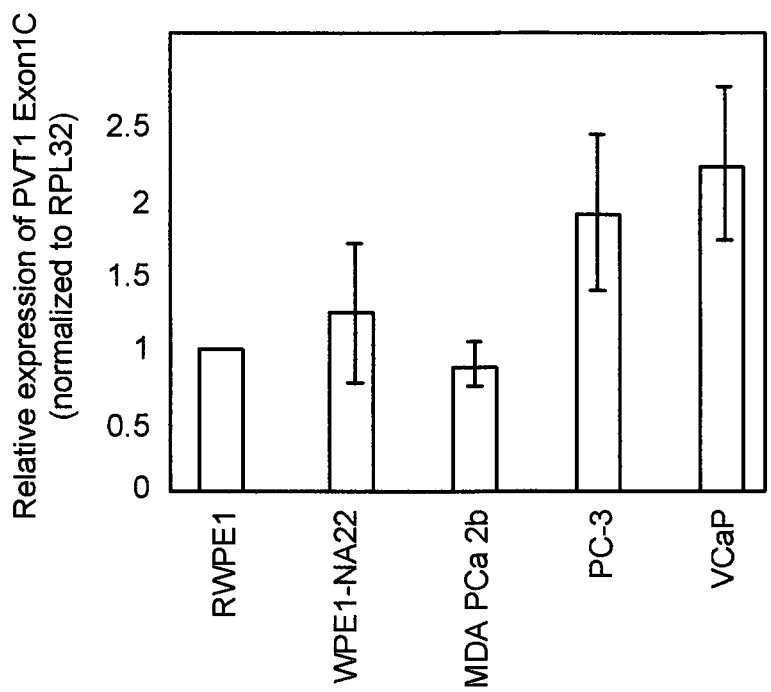

FIG. 2A, FIG. 2B and FIG. 2C depict expression of PVT1 exons 1a; 1b and 1c in non-tumorigenic and tumorigenic prostate epithelial cell lines. Four independent qPCR experiments were performed and every experiment was set up in quadruplicates. The data showed that there is no significant differential expression of the exons in the cell lines in comparing cell lines derived from CM with those derived from MoAA. The data are presented as mean+standard error of the mean (SEM).

Figure 3A:
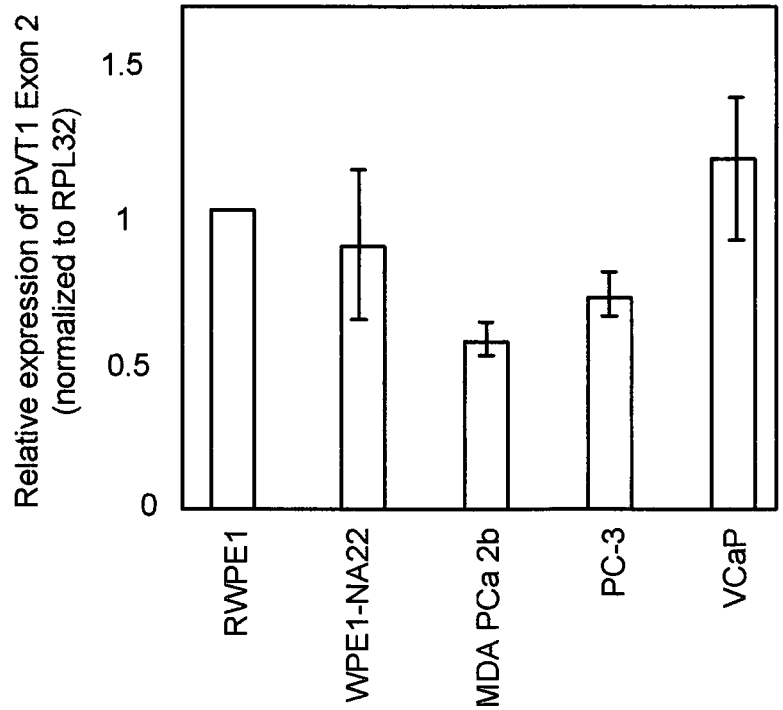
FIG. 3A, FIG. 3B and FIG. 3C are graphs depicting expression of PVT1 exons 2; 3b and 4a in non-tumorigenic and tumorigenic prostate epithelial cell lines.
Figure 3B:
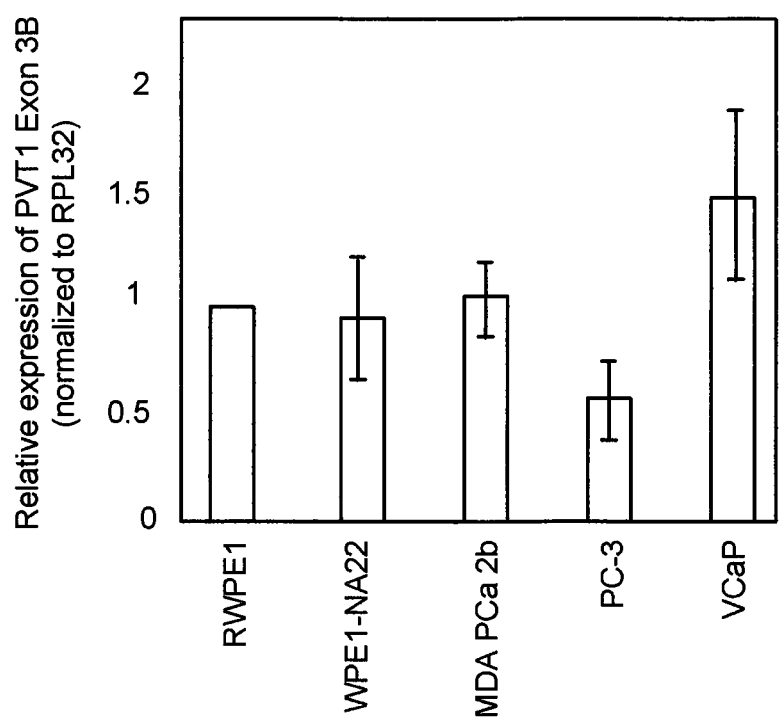
Figure 3C:
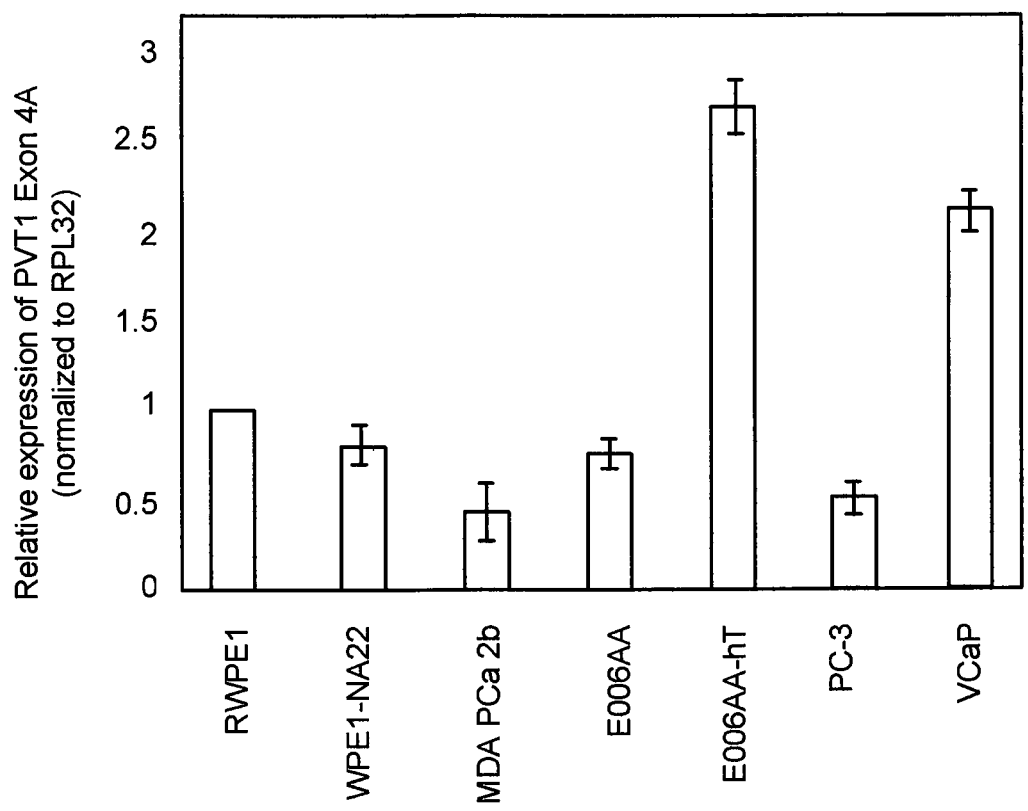
Figure 4C:
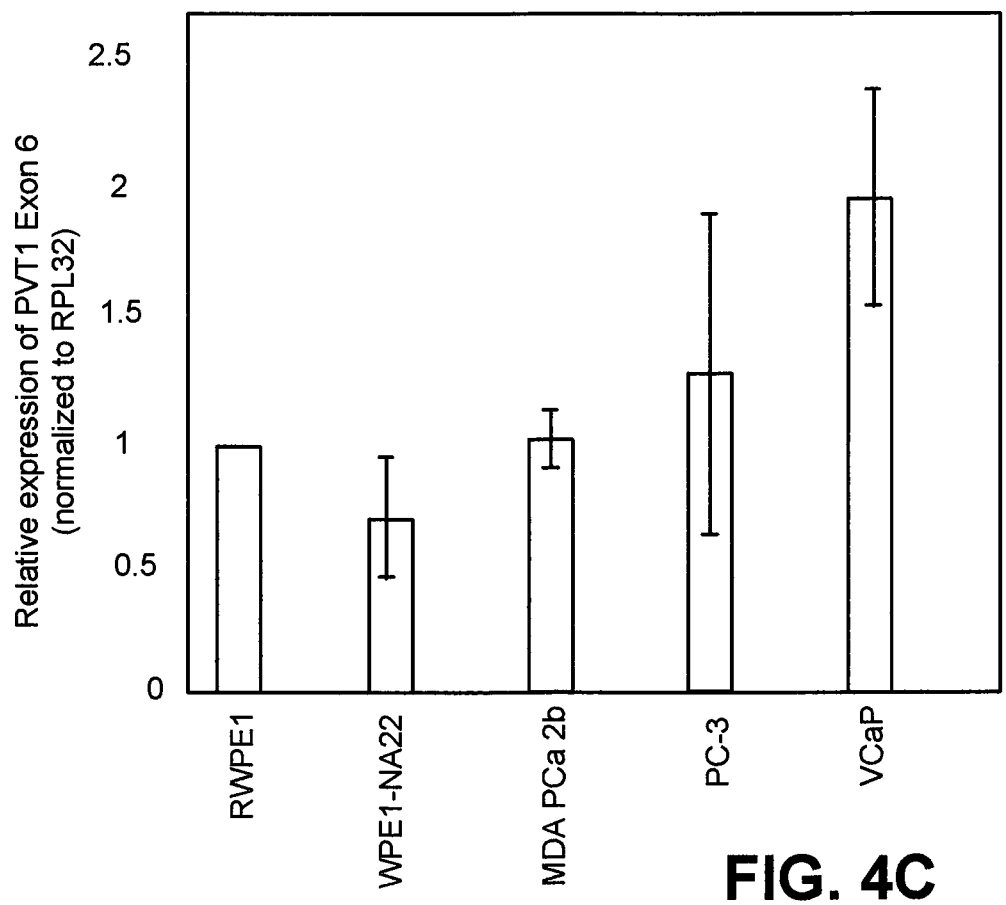

FIG. 3A, FIG. 3B and FIG. 3C depict PVT1 exons 2; 3b and 4a expression in non-tumorigenic and tumorigenic prostate epithelial cell lines. Four (for exon 2 and exon 3b) or 3 (for exon 4a) independent qPCR experiments were performed and every experiment was set up in quadruplicates. The data showed that there is no significant differential expression of the exons in the cell lines in comparing cell lines derived from CM with those derived from MoAA. The data are presented as mean±standard error of the mean (SEM).

FIG. 4A to FIG. 5B depict expression of PVT1 exons 4b, 5, 6 (FIG. 4A, FIG. 4B and FIG. 4C) and exons 7 and 8 (FIG. 5A and FIG. 5B). There were no differential expression observed in comparing MDA PCa 2b to RWPE1. PVT1 exons 4b (FIG. 4A); 5 (FIG. 4B) and 6 (FIG. 4C) expression in non-tumorigenic and tumorigenic prostate epithelial cell lines. Four independent qPCR experiments were performed and every experiment was set up in quadruplicates. The data showed that there was no significant differential expression of the exons in the cell lines in comparing cell lines derived from CM with those derived from MoAA. The data are presented as mean+standard error of the mean (SEM). PVT1 exons 7 (FIG. 5A) and 8 (FIG. 5B) expression in non-tumorigenic and tumorigenic prostate epithelial cell lines. Four independent qPCR experiments were performed and every experiment was set up in quadruplicates. The data showed that there is no significant differential expression of the exons in the cell lines in comparing cell lines derived from CM with those derived from MoAA. The data are presented as mean+standard error of the mean (SEM).

Figure 6:
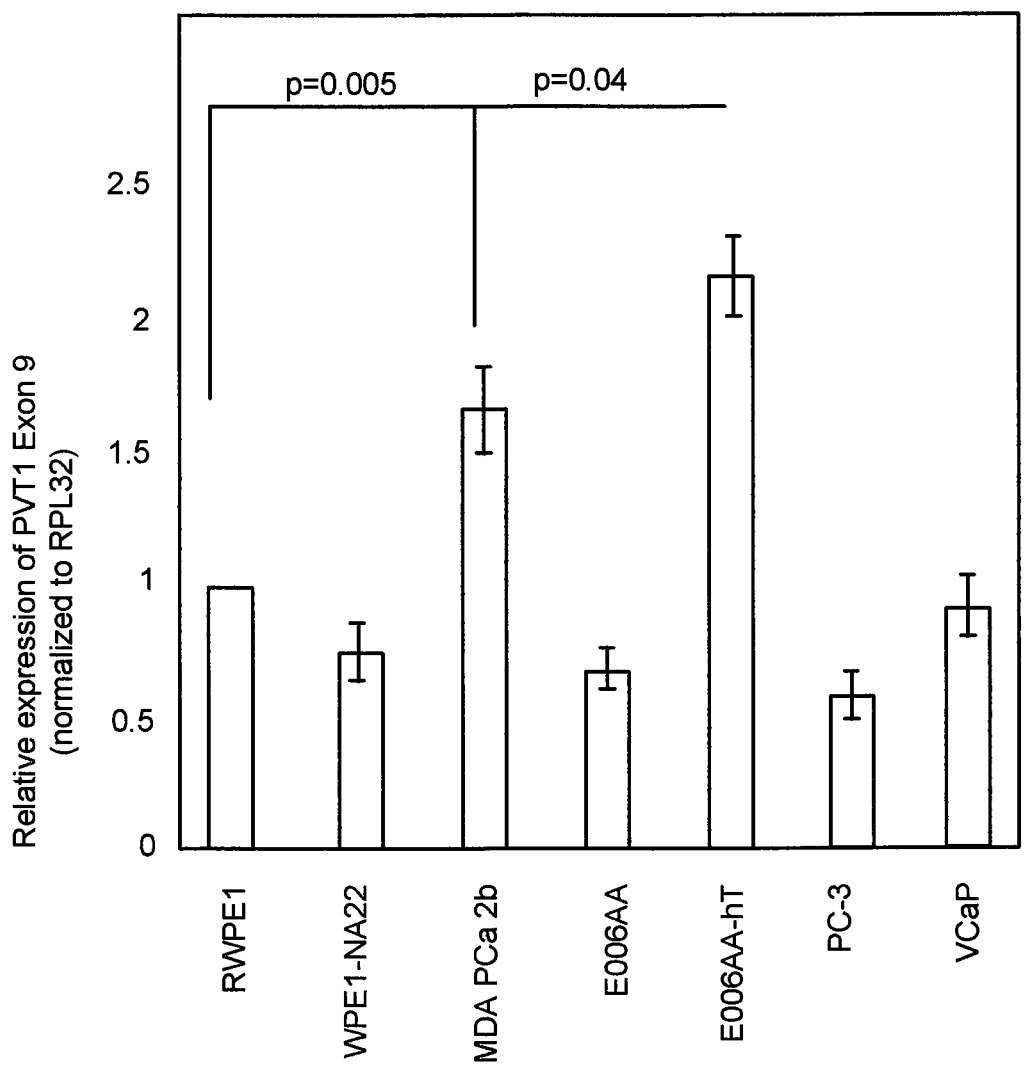
FIG. 6 is a graph depicting PVT1 exon 9 overexpression in aggressively tumorigenic PCa cell line from males of African ancestry.

FIG. 6 depicts PVT1 exon 9 overexpression in aggressively tumorigenic PCa cell line from MoAA. Five independent qPCR experiments were performed and every experiment was set up in quadruplicates. The data showed that PVT1 exon 9 is consistently significantly overexpressed in the aggressive PCa cell lines derived from MoAA in comparison to the non-tumorigenic PCa cell line it was derived from. The data are presented as mean+standard error of the mean (SEM) and the p values are displayed on FIG. 6. The lower panel shows the different prostate cell lines' PVT1 exon 9 PCR products loaded on a 0.8% agarose gel.

Figure 7:
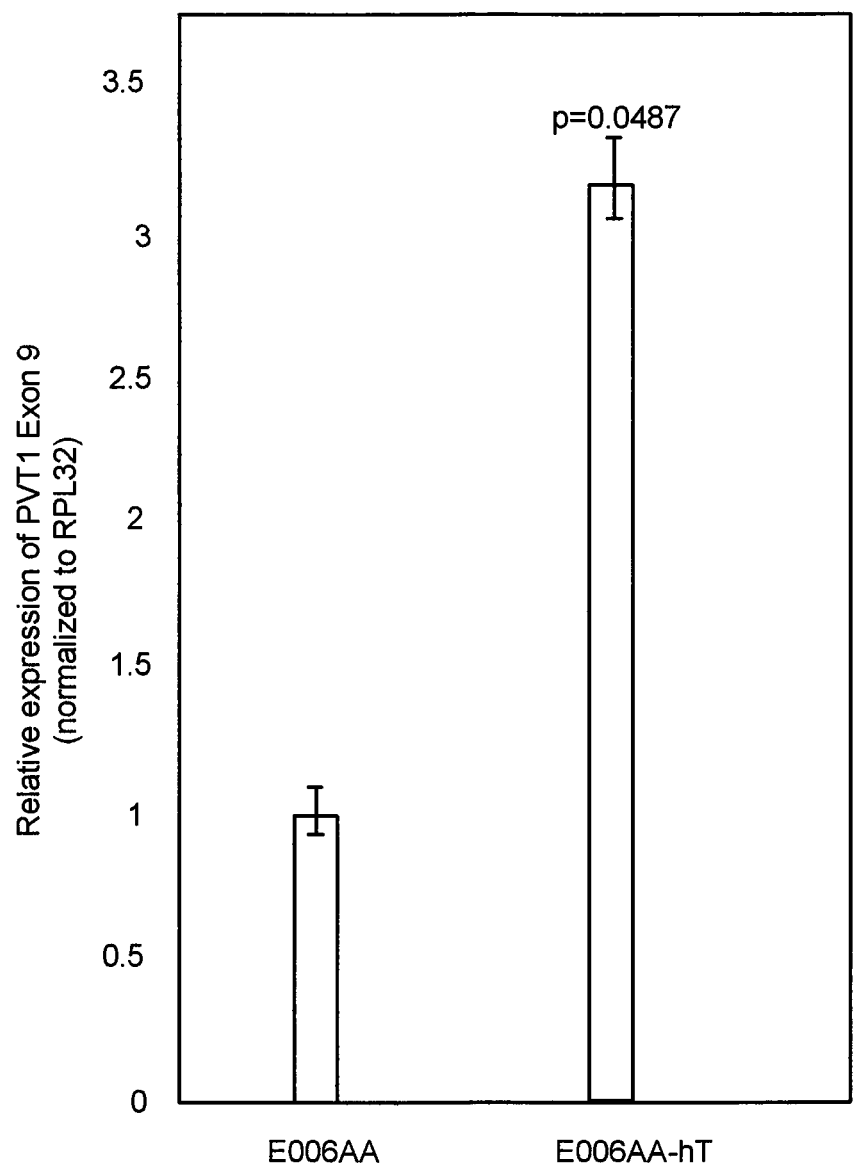
FIG. 7 is a graph depicting PVT exon 9 expression in non-tumorigenic and tumorigenic prostate epithelial cell lines.

PVT1 exon 9 was the only one of all twelve exons of PVT1 that showed a very consistent and easily explainable expression profile. PVT1 exon 9 was significantly and consistently overexpressed in both aggressively tumorigenic cell lines derived from men of African ancestry. In both MDA PCa 2b and E006AA-hT cell lines, relative expression of PVT1 exon 9 in comparison to the RWPE1 cell line were approximately 200% (two-fold) higher (FIG. 6). Interestingly, in comparing the E006AA non-tumorigenic cell line derived from a MoAA with its derivative, the aggressively tumorigenic E006AA-hT cell line, PVT1 exon 9 expression was about 300% higher in the E006AA-hT cell line (p=0.0487; FIG. 7). This indicates that PVT1 exon 9 is related to aggressiveness in this model of PCa in a MoAA.

FIG. 7 depicts PVT1 exon 9 expression in non-tumorigenic and tumorigenic prostate epithelial cell lines. At least three independent qPCR experiments were performed and every experiment was set up in quadruplicates. The data showed that PVT1 exon 9 is consistently significantly overexpressed in the aggressive PCa cell lines derived from MoAA. The data are presented as mean±standard error of the mean (SEM) and the p values are displayed on FIG. 7, and are compared to the control (RWPE1 cell line).

The long non-protein coding RNA (lncRNA) PVT1 has been shown to be important in cancer. PVT1 overexpression has been demonstrated in pancreatic cancer and colon cancer, and is related to poor prognosis in most of these cases. However, these studies did not distinguish between the different transcripts of PVT1. It is possible that the different exons of PVT1 could be differentially expressed, and have different functions. Here, a study was performed where primers were annotated and designed for amplification of twelve separate exons of PVT1. The results show that most of the exons do not have differential expression in PCa. However, very interestingly, one particular exon of PVT1, PVT1 exon 9, was consistently and significantly overexpressed in the aggressive PCa cell lines derived from MoAA. Importantly, PVT1 exon 9 is demonstrated to be significantly overexpressed in the aggressive PCa cell line derived from a MoAA in comparison to its non-tumorigenic cell line from which it was derived. This clearly indicates that PVT1 exon 9 overexpression is significantly associated with aggressiveness in this model of PCa in a MoAA. Whether this will translate to individuals or subpopulations at risk prospectively is at present unknown. A more in depth evaluation of prospectively collected PCa gene databases and fresh prostate specimens will be required to understand whether this phenomenon can be used as a biomarker for MoAA with PCa. Already, emerging data from an ongoing clinical study strongly indicates that PVT1 exon 9 is overexpressed in prostate tumor tissue in comparison to benign prostate tissue, and even much more so in comparison to normal prostate tissue.

The physical characteristics of the custom-designed PVT1 exon 9 primers are as follows: the disclosed PVT1 exon 9 primers amplify a region of 210 bp in the PVT1 exon 9 sequence. In order to design PVT1 exon 9 primers, the PVT1 exon 9 sequence shown below was used.

The PVT1 exon 9 sequence is given by:
(SEQ ID NO: 25)
GTTTTTTGCATGTCTGACACCCATGACTCCACCTGGACCTTATGGCTCCA

CCCAGAAGCAATTCAGCCCAACAGGAGGACAGCTTCAACCCATTACGATT

TCATCTCTGCCCCAACCACTCAGCAGCAAGCACCTGTTACCTGTCCACCC

CCACCCCTTCCCCCAAACTGCCTTTGAAAAATCCCTAACCTATGAGCTTT

GAATAAGATGAGTACGAACTTCATCGCCCACGTGGCGTGGCCGGCCTCGT

GTCTATTAAATTCTTTTTCTACT

The corresponding forward and reverse primers designed are given as SEQ ID NO: 23 and SEQ ID NO: 24.

To determine if a lncRNA is important, its cellular functions need to be elucidated. It will be important to determine if the lncRNA regulates important cellular functions or if it just represents "transcriptional noise" or background transcription. Although lncRNAs are sometimes aberrantly expressed in diseased tissues, suggesting specific functions in diseases, knowledge of how these lncRNA act in the cell and which roles they might play in diseases in still very limited. Therefore, an understanding of the cellular functions, mechanisms of action, and mechanisms regulating PVT1 exon 9 expression will be critical to exploiting it for potential clinical applications.

siRNAs as Inhibitors

Five different siRNAs were custom-designed specifically targeting PVT1 exon 9. As PVT1 exon 9 had not been previously described in literature, there were no siRNAs to PVT1 exon 9 available. These five new custom-designed PVT1 exon 9 siRNAs are very valuable tools that are very useful in understanding the function of PVT1 exon 9 in prostate cancer. Data show that these siRNAs may have therapeutic application in prostate cancer. The sequences and main characteristics of all duplexes are shown in Table 4A and Table 4B.

TABLE 4A

| Oligo Name | Sequence (5'-3') |
|---|---|
| PVT1 exon9_siRNA 1F | CUUCAACCCAUUACGAUUUUU (SEQ ID NO: 26) |
| PVT1 exon9_siRNA 1R | AAAUCGUAAUGGGUUGAAGUU (SEQ ID NO: 27) |
| PVT1 exon9_siRNA 2F | GGACAGCUUCAACCCAUUAUU (SEQ ID NO: 28) |
| PVT1 exon9_siRNA 2R | UAAUGGGUUGAAGCUGUCCUU (SEQ ID NO: 29) |

TABLE 4A-continued

| Oligo Name | Sequence (5'-3') |
|---|---|
| PVT1 exon9_siRNA 3F | AGGACAGCUUCAACCCAUUUU (SEQ ID NO: 30) |
| PVT1 exon9_siRNA 3R | AAUGGGUUGAAGCUGUCCUUU (SEQ ID NO: 31) |
| PVT1 exon9_siRNA 4F | CCAUUACGAUUUCAUCUCUUU (SEQ ID NO: 32) |
| PVT1 exon9_siRNA 4R | AGAGAUGAAAUCGUAAUGGUU (SEQ ID NO: 33) |
| PVT1 exon9_siRNA 5F | ACCUAUGAGCUUUGAAUAAUU (SEQ ID NO: 34) |
| PVT1 exon9_siRNA 5R | UUAUUCAAAGCUCAUAGGUUU (SEQ ID NO: 35) |

TABLE 4B

| Oligo Name | Length | m.w. | Tm | Dimers | Secondary structure | GC % |
|---|---|---|---|---|---|---|
| PVT1 exon9_siRNA 1F | 21 | 13278 | 50.5 | No | None | 33.3 |
| PVT1 exon9_siRNA 1R | 21 | 13278 | 50.5 | No | None | 33.3 |
| PVT1 exon9_siRNA 2F | 21 | 13308 | 58.1 | No | None | 42.8 |
| PVT1 exon9_siRNA 2R | 21 | 13308 | 58.1 | No | Very weak | 42.8 |
| PVT1 exon9_siRNA 3F | 21 | 13308 | 59.5 | No | None | 42.8 |
| PVT1 exon9_siRNA 3R | 21 | 13308 | 59.5 | No | Very weak | 42.8 |
| PVT1 exon9_siRNA 4F | 21 | 13278 | 50.1 | No | Very weak | 33.3 |
| PVT1 exon9_siRNA 4R | 21 | 13278 | 50.1 | No | Very weak | 33.3 |
| PVT1 exon9_siRNA 5F | 21 | 13263 | 49.9 | Yes | None | 28.5 |
| PVT1 exon9_siRNA 5R | 21 | 13263 | 49.9 | No | None | 28.5 |

In one embodiment, the sequences disclosed in Table 4A comprise an overhang on their 3' end.

The immediate application PVT1 exon 9 siRNAs is the silencing of PVT1 exon 9 endogenous expression in cells in order to study the effects of loss of expression of PVT1 exon 9 on various cellular functions. The data indicate that these PVT1 exon 9 siRNAs may have therapeutic potential in aggressive prostate cancer. Silencing of PVT1 exon 9 expression using these siRNAs resulted in induction of apoptosis, cell cycle arrest at G1 phase, dephosphorylation of the retinoblastoma protein, and loss of expression of the proliferating cell nuclear antigen (PCNA) protein.

Figure 8:
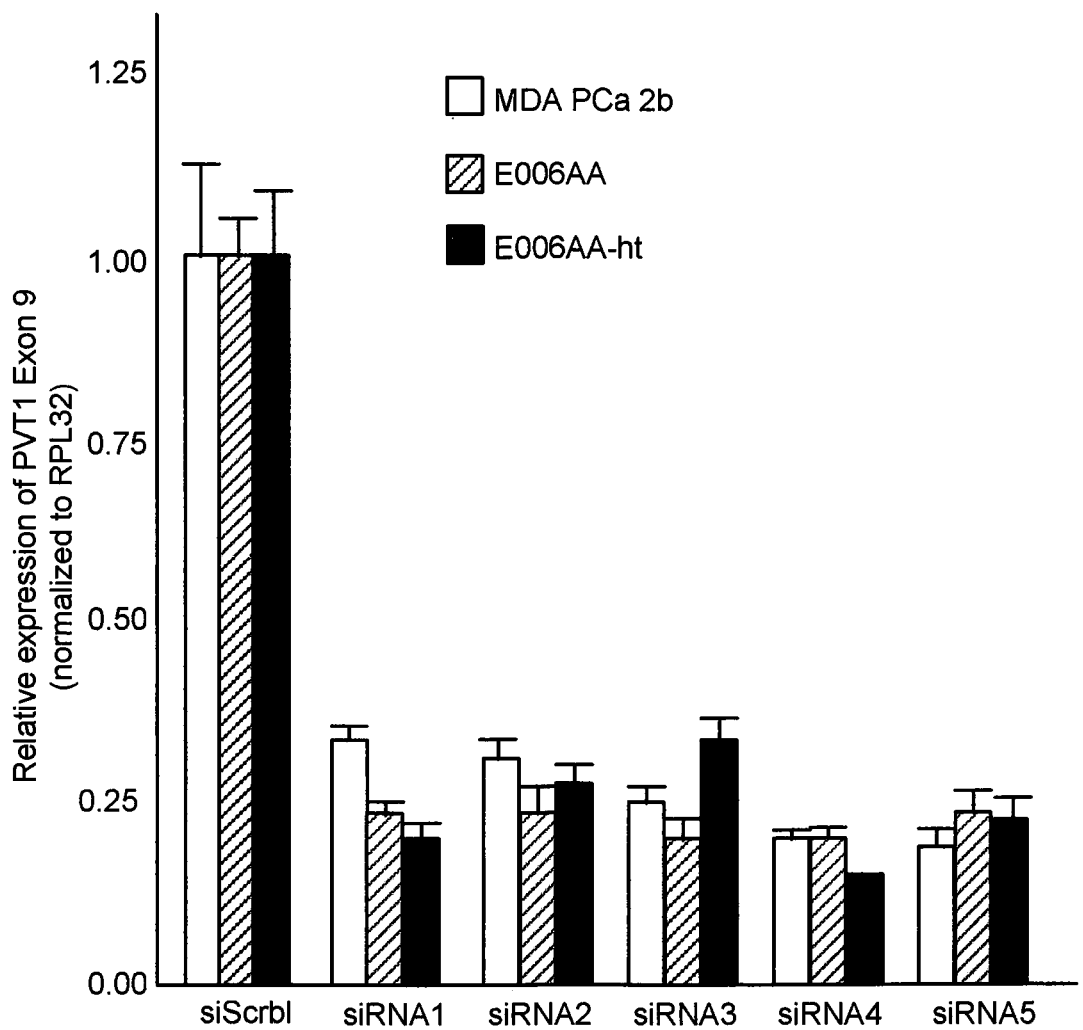
FIG. 8 is a graph depicting expression of PVT1 exon 9 on select PCa cell lines that are exposed to the five siRNAs.

FIG. 8 depicts expression of PVT1 exon 9 (relative to RPL32) on select PCa cell lines that are exposed to the five siRNAs. Cells were transfected with 30 pM siRNA for 72 hours. FIG. 8 shows the response of MDA PCa 2b, E006AA and E006AA-hT cell lines exposed to siRNA 1, siRNA 2, siRNA3, siRNA4 or siRNA5. A control (siScrbl) scrambled sequence is also provided.

Figure 9:
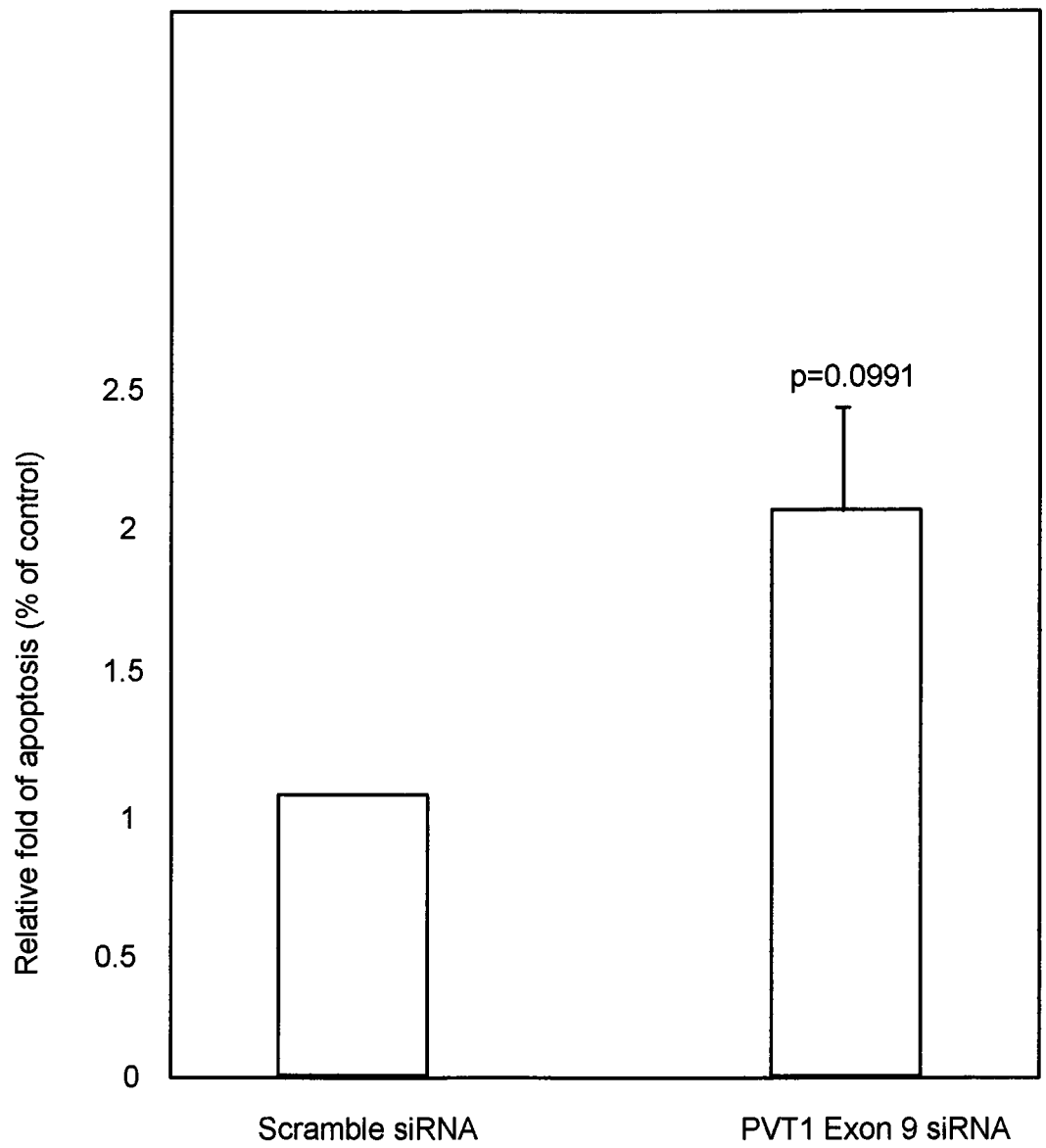
FIG. 9 is a graph depicting the relative fold of apoptosis induced by select siRNAs.

FIG. 9 is a graph depicting the relative fold of apoptosis (as a percent of control) induced by select siRNA5. The data indicates a two-fold increase in apoptosis when 30 pM siRNA5 is utilized.

Figure 10:
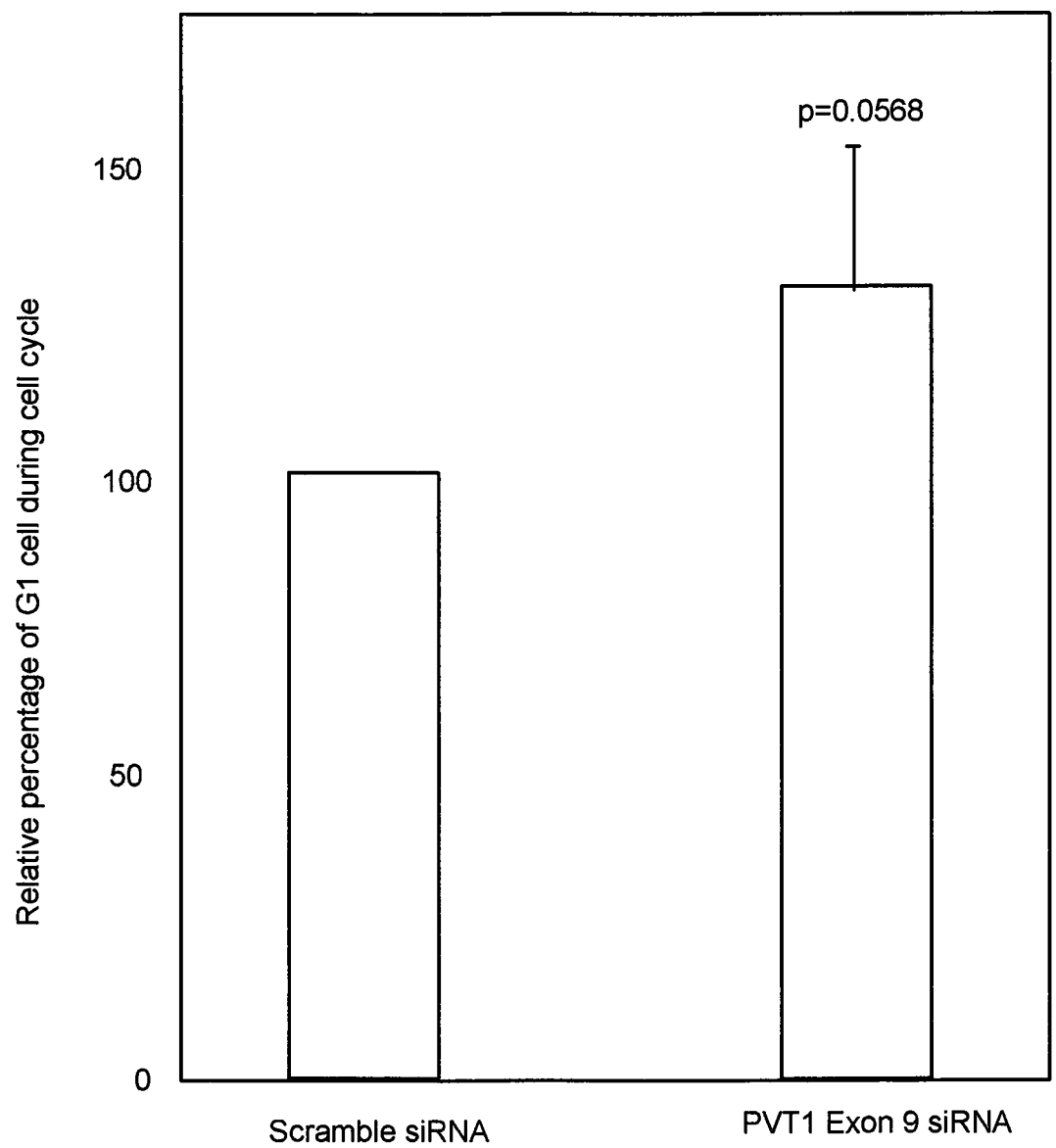
FIG. 10 is a graph showing the siRNAs arrest cell cycle progression at the G1 phase of the cell cycle.

FIG. 10 is a graph showing the effect of 30 pM siRNA5 in inducing arrest of E006AA-hT PCa cells at the G1 phase of cell cycle.

Figure 11:
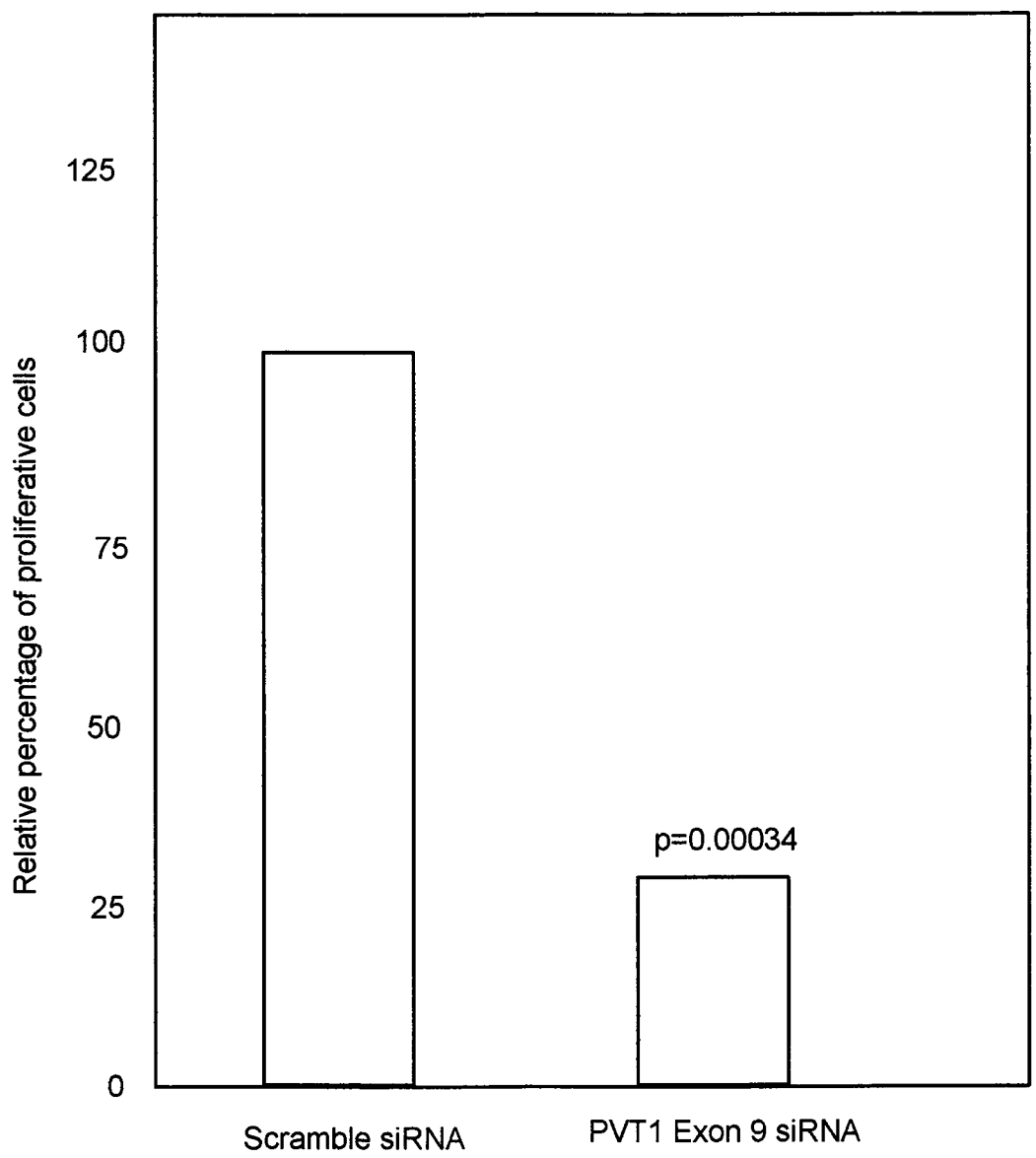
FIG. 11 is a graph depicting relative percentage of proliferative cells when exposed to a select siRNA.
Figure 12:
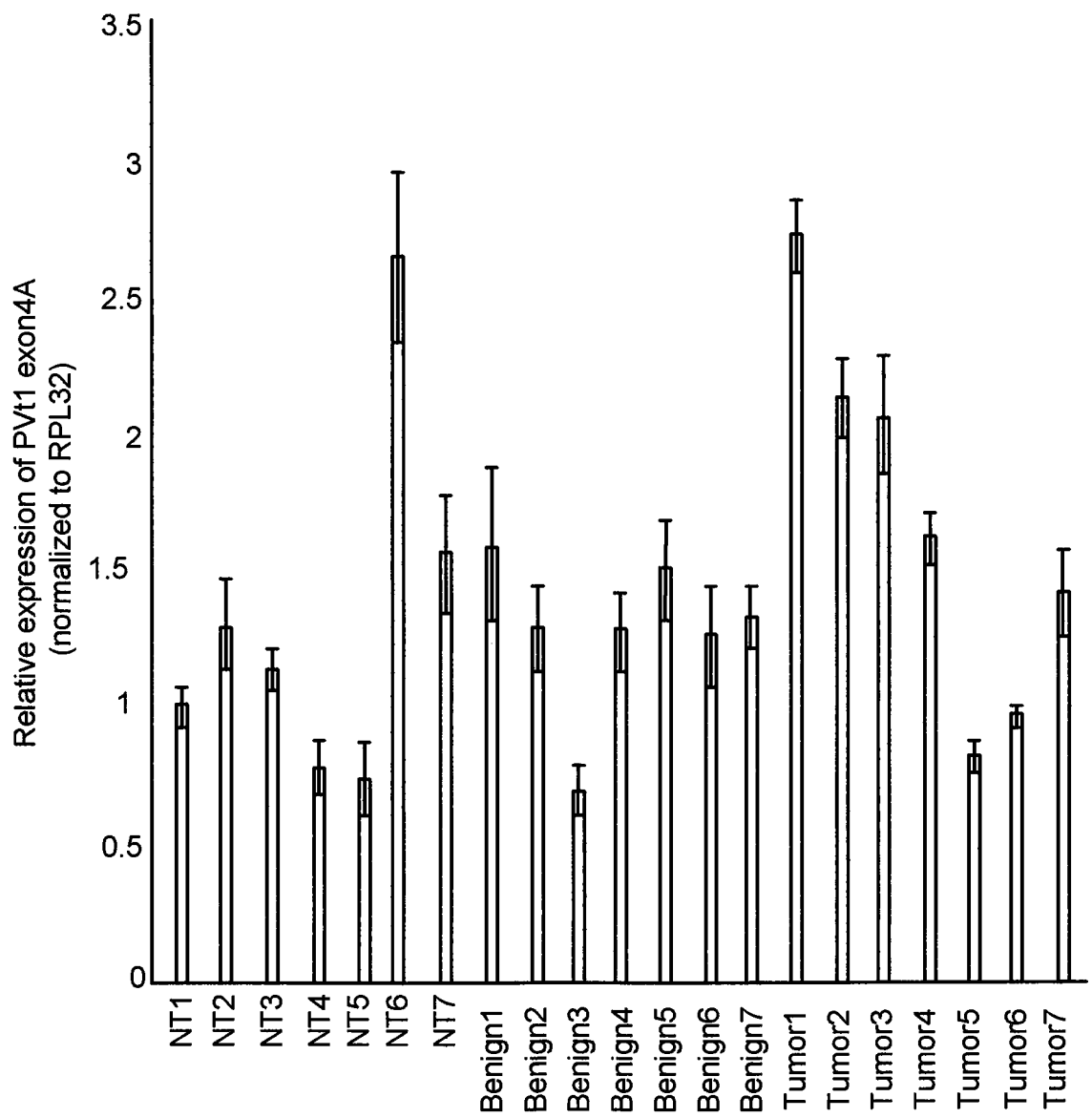
FIG. 12 is a graph showing relative expression of PVT1 exon 4a in various prostate tissues.

FIG. 11 is a graph showing the relative percentage of proliferative cells after treatment with 30 pM siRNA5 on the E006AA-hT PCa cell line after 72 hours;

FIG. 12 is a graph showing relative expression of PVT1 exon 4a of seven benign prostate tissues; seven prostate tumor tissues and seven normal prostate tissues. Total RNA were extracted from human prostate tissue; seven samples of normal prostate tissue (NT), seven samples from benign prostate tissue and seven samples of prostate tumor tissues. Synthesis of cDNA were performed with 450 ng of RNA.

Figure 13:
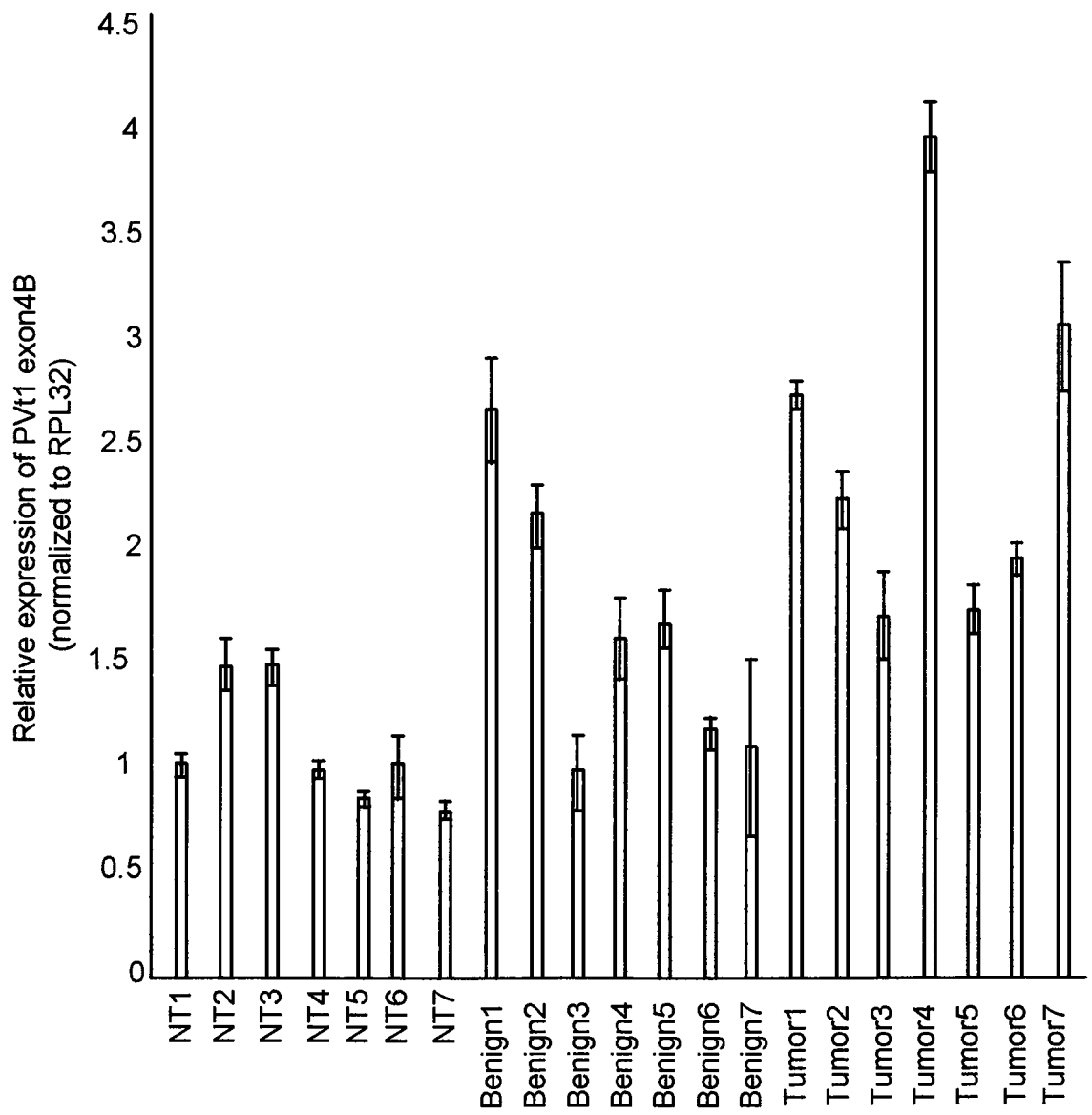
FIG. 13 is a graph showing relative expression of PVT1 exon 4b in various prostate tissues.

FIG. 13 is a graph showing relative expression of PVT1 exon 4b in seven benign prostate tissues; seven prostate tumor tissues and seven normal prostate tissues.

Figure 14:
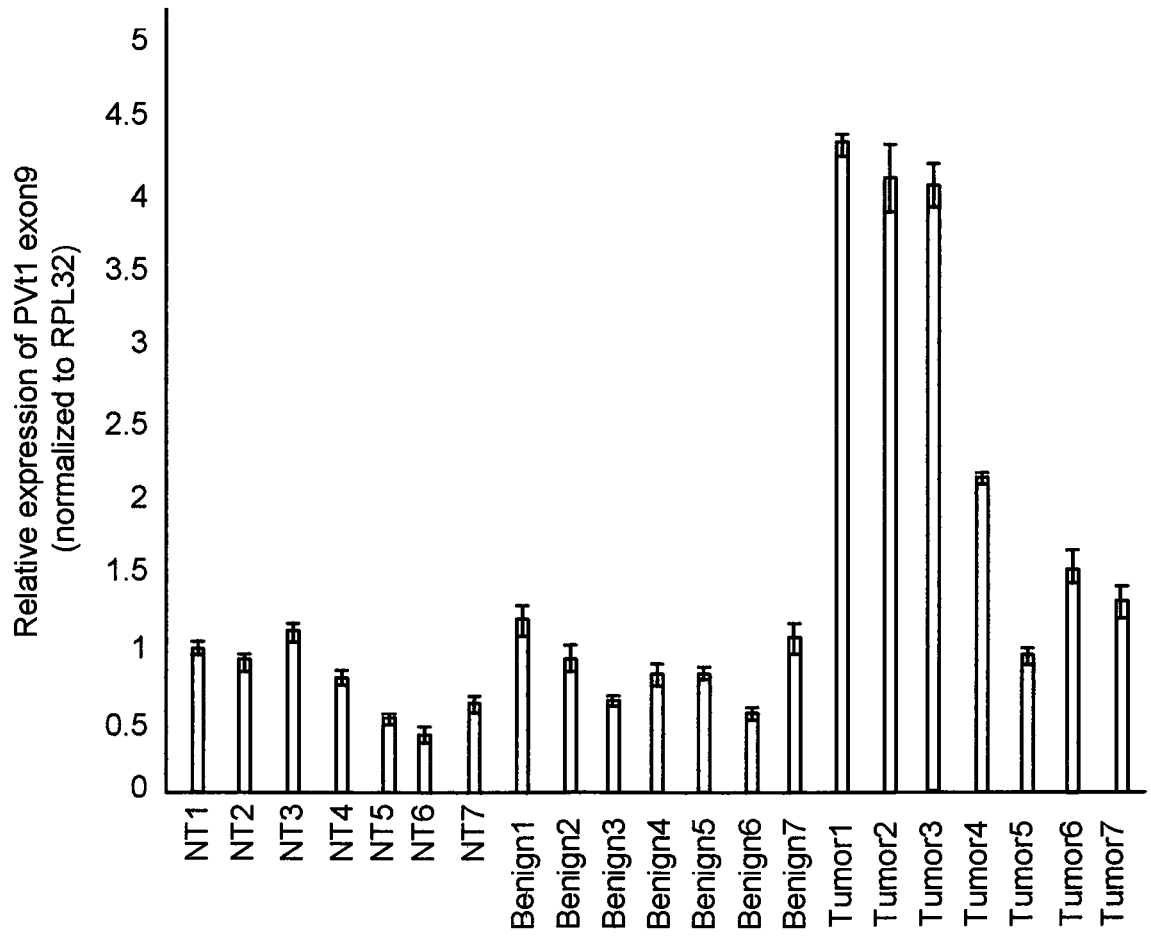
FIG. 14 is a graph showing relative expression of PVT1 exon 9 in various prostate tissues.

FIG. 14 is a graph showing relative expression of PVT1 exon 9 in seven benign prostate tissues; seven prostate tumor tissues and seven normal prostate tissues.

In one embodiment, a small interfering ribonucleic acid (siRNA) is provided that comprises a double stranded siRNA with fewer than twenty-six nucleotides. The double stranded siRNA comprises a first strand comprising a primary structure and a first 3' overhang, the primary structure being selected from the group consisting of CUUCAACC-CAUUACGAUUU (SEQ ID NO. 26); GGACAGCUU-CAACCCAUUA (SEQ ID NO. 28); AGGACAGCUU-CAACCCAUU (SEQ ID NO. 30); CCAUUACGAUUUCAUCUCU (SEQ ID NO. 32); and ACCUAUGAGCUUUGAAUAA (SEQ ID NO. 34). The siRNA further comprises a second strand that is complementary to the first strand, the second strand having a second 3' overhang. In one embodiment, the first 3' overhang is UU and the second 3' overhang is UU. In another embodiment, the double stranded siRNA has twenty-one nucleotides. In another embodiment, the first 3' overhang is UU and the second 3' overhang is UU and the double stranded siRNA has twenty-one nucleotides.

In another embodiment a method of treating aggressive prostate cancer is disclosed. The method comprises administering to a prostate tumor a small interfering ribonucleic acid (siRNA) comprising a double stranded siRNA with fewer than twenty-six nucleotides, the double stranded siRNA comprising: a first strand comprising a primary structure and a first 3' overhang, the primary structure being selected from the group consisting of CUUCAACC-CAUUACGAUUU (SEQ ID NO. 26); GGACAGCUU-CAACCCAUUA (SEQ ID NO. 28); AGGACAGCUU-CAACCCAUU (SEQ ID NO. 30); CCAUUACGAUUUCAUCUCU (SEQ ID NO. 32); and ACCUAUGAGCUUUGAAUAA (SEQ ID NO. 34). The siRNA comprises a second strand that is complementary to the first strand, the second strand having a second 3' overhang.

The PVT1 exon 4A sequence is given by:
(SEQ ID NO: 36)
AGTCTCACTCTGTGGTCCAGGCTGAAGTACAGTGGCATGATCCCAGGTCA

CTGCAACCCCCACCTCCCGGGTTCAAGTGATCCTCCTGCCTCAGCCTCCC

GAGTAGCTGGTATTACAGGCGTGTGCCACAAAGCCTGGCTAAGTTTTGTA

TTTTTAGTAGAGACGGGGTTTCACCATGTTGGCCAGGTTGGTCTCGAACT

CCTGACCTCAAGTGATCCACTCACTTTGGCCTTTCAACGTGCTGGGATTA

CAGGCGAGAGTCACCGCACCCGGACGACTCTGACATTTTTGAAGAGTCCA

G.

The PVT1 exon 4B sequence is given by:
(SEQ ID NO: 37)
AATCCTGTTACACCTGGGATTTAGGCACTTTCAATCTGAAAAAATACATA

TCCTTTCAGCACTCTGGACGGACTTGAGAACTGTCCTTACGTGACCTAAA

GCTGGAGTATTTTGAGATTGGAGAATTAAG

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of producing an analyte, the method comprising sequential steps of:
   obtaining a sample of prostate tissue;
   extracting ribonucleic acid (RNA) from the prostate tissue;
   performing quantitative polymerase chain reaction (qPCR) on the RNA to amplify a PVT1 exon 4A sequence given by SEQ ID NO: 36 or a PVT1 exon 4B sequence given by SEQ ID NO. 37, the qPCR generating replicated fragments that are useful as analytes.

2. The method recited in claim 1, further comprising steps of
   quantifying a concentration of the replicated fragments;
   comparing the concentration of the replicated fragments to a predetermined threshold concentration, wherein the prostate tissue is deemed to be aggressive prostate cancer if the concentration exceeds the predetermined threshold.

3. The method as recited in claim 2, wherein the step of performing quantitative polymerase chain reaction (qPCR) utilizes a forward primer with a sequence given by SEQ ID NO. 11 and a reverse primer with a sequence given by SEQ ID NO. 12.

4. The method as recited in claim 2, wherein the step of performing quantitative polymerase chain reaction (qPCR) utilizes a forward primer with a sequence given by SEQ ID NO. 13 and a reverse primer with a sequence given by SEQ ID NO. 14.

* * * * *